(12) United States Patent
Shankarsetty et al.

(10) Patent No.: US 11,065,000 B2
(45) Date of Patent: Jul. 20, 2021

(54) SURGICAL BUTTRESSES FOR SURGICAL STAPLING APPARATUS

(71) Applicant: Covidien LP, Mansfield, MA (US)

(72) Inventors: Jeevan Maddur Shankarsetty, Bangalore (IN); Hari Naga Mahesh Kalepu, Hyderabad (IN); Jitendra Bhargava Srinivas, Hyderabad (IN)

(73) Assignee: COVIDIEN LP, Mansfield, MA (US)

( * ) Notice: Subject to any disclaimer, the term of this patent is extended or adjusted under 35 U.S.C. 154(b) by 139 days.

(21) Appl. No.: 16/265,299

(22) Filed: Feb. 1, 2019

(65) Prior Publication Data

US 2019/0254671 A1   Aug. 22, 2019

Related U.S. Application Data

(60) Provisional application No. 62/633,747, filed on Feb. 22, 2018.

(51) Int. Cl.
*A61B 17/072* (2006.01)
*A61B 17/00* (2006.01)
*A61B 17/06* (2006.01)

(52) U.S. Cl.
CPC ............ *A61B 17/07292* (2013.01); *A61B 2017/00477* (2013.01); *A61B 2017/00951* (2013.01);
(Continued)

(58) Field of Classification Search
CPC .... A61B 17/07292; A61B 2017/00951; A61B 2017/06176; A61B 2017/00477;
(Continued)

(56) References Cited

U.S. PATENT DOCUMENTS 3,054,406 A   9/1962   Usher
3,124,136 A   3/1964   Usher
(Continued)

FOREIGN PATENT DOCUMENTS

CA   2282761 A1   9/1998
DE   1602563 U   3/1950
(Continued)

OTHER PUBLICATIONS

Partial European Search Report dated May 27, 2019 corresponding to counterpart Patent Application EP 19158469.7.
(Continued)

*Primary Examiner* — Robert F Long

(57) ABSTRACT

A surgical stapling apparatus includes an end effector having an anvil assembly and a staple cartridge assembly, and an anvil buttress retention system releasably disposed on the anvil assembly. The anvil buttress retention system includes an anvil buttress and a retention member including an elongated body looped around at least a portion of the anvil buttress with a free end of the elongated body extendable through a looped end of the elongated body in an untightened configuration such that the anvil buttress retention system is slidable relative to the anvil assembly. The free end of the retention member is movable relative to and through the looped end to a tightened configuration to secure the anvil buttress retention system to the anvil assembly.

10 Claims, 8 Drawing Sheets

(52) U.S. Cl.
CPC ............... *A61B 2017/06176* (2013.01); *A61B 2017/07257* (2013.01); *A61B 2017/07271* (2013.01); *A61B 2017/07285* (2013.01)

(58) Field of Classification Search
CPC  A61B 2017/07257; A61B 2017/07271; A61B 2017/07285
USPC .......................................... 227/175.1–182.1
See application file for complete search history.

(56) References Cited

U.S. PATENT DOCUMENTS

| | | |
|---|---|---|
| 3,364,200 A | 1/1968 | Ashton et al. |
| 3,499,591 A | 3/1970 | Green |
| 3,797,494 A | 3/1974 | Zaffaroni |
| 3,939,068 A | 2/1976 | Wendt et al. |
| 3,948,666 A | 4/1976 | Kitanishi et al. |
| 4,064,062 A | 12/1977 | Yurko |
| 4,166,800 A | 9/1979 | Fong |
| 4,282,236 A | 8/1981 | Broom |
| 4,347,847 A | 9/1982 | Usher |
| 4,354,628 A | 10/1982 | Green |
| 4,416,698 A | 11/1983 | McCorsley, III |
| 4,429,695 A | 2/1984 | Green |
| 4,452,245 A | 6/1984 | Usher |
| 4,605,730 A | 8/1986 | Shalaby et al. |
| 4,626,253 A | 12/1986 | Broadnax, Jr. |
| 4,655,221 A | 4/1987 | Devereux |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,057,334 A | 10/1991 | Vail |
| 5,065,929 A | 11/1991 | Schulze et al. |
| 5,112,496 A | 5/1992 | Dhawan et al. |
| 5,162,430 A | 11/1992 | Rhee et al. |
| 5,205,459 A | 4/1993 | Brinkerhoff et al. |
| 5,263,629 A | 11/1993 | Trumbull et al. |
| 5,281,197 A | 1/1994 | Arias et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,324,775 A | 6/1994 | Rhee et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,405,072 A | 4/1995 | Zlock et al. |
| 5,410,016 A | 4/1995 | Hubbell et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,468,253 A | 11/1995 | Bezwada et al. |
| 5,484,913 A | 1/1996 | Stilwell et al. |
| 5,503,638 A * | 4/1996 | Cooper ............ A61B 17/07207 606/148 |
| 5,514,379 A | 5/1996 | Weissleder et al. |
| 5,542,594 A | 8/1996 | McKean et al. |
| 5,543,441 A | 8/1996 | Rhee et al. |
| 5,549,628 A | 8/1996 | Cooper et al. |
| 5,550,187 A | 8/1996 | Rhee et al. |
| 5,575,803 A | 11/1996 | Cooper et al. |
| 5,645,915 A | 7/1997 | Kranzler et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A * | 12/1997 | Rayburn .......... A61B 17/07207 227/176.1 |
| 5,752,965 A | 5/1998 | Francis et al. |
| 5,752,974 A | 5/1998 | Rhee et al. |
| 5,762,256 A | 6/1998 | Mastri et al. |
| 5,766,188 A * | 6/1998 | Igaki ................ A61B 17/07207 606/139 |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,819,350 A | 10/1998 | Wang |
| 5,833,695 A | 11/1998 | Yoon |
| 5,843,096 A | 12/1998 | Igaki et al. |
| 5,871,135 A | 2/1999 | Williamson, IV et al. |
| 5,874,500 A | 2/1999 | Rhee et al. |
| 5,895,412 A | 4/1999 | Tucker |
| 5,895,415 A | 4/1999 | Chow et al. |
| 5,902,312 A * | 5/1999 | Frater ............... A61B 17/07207 606/148 |
| 5,908,427 A | 6/1999 | McKean et al. |
| 5,915,616 A | 6/1999 | Viola et al. |
| 5,931,847 A | 8/1999 | Bittner et al. |
| 5,957,363 A | 9/1999 | Heck |
| 5,964,394 A | 10/1999 | Robertson |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,093,557 A | 7/2000 | Pui et al. |
| 6,099,551 A * | 8/2000 | Gabbay ............ A61B 17/07207 227/176.1 |
| 6,142,933 A | 11/2000 | Longo et al. |
| 6,149,667 A | 11/2000 | Hovland et al. |
| 6,152,943 A | 11/2000 | Sawhney |
| 6,155,265 A | 12/2000 | Hammerslag |
| 6,156,677 A | 12/2000 | Brown Reed et al. |
| 6,165,201 A | 12/2000 | Sawhney et al. |
| 6,179,862 B1 | 1/2001 | Sawhney |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,270,530 B1 | 8/2001 | Eldridge et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,309,569 B1 | 10/2001 | Farrar et al. |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,330,965 B1 | 12/2001 | Milliman et al. |
| 6,399,362 B1 | 6/2002 | Pui et al. |
| 6,436,030 B2 | 8/2002 | Rehil |
| 6,454,780 B1 | 9/2002 | Wallace |
| 6,461,368 B2 | 10/2002 | Fogarty et al. |
| 6,500,777 B1 | 12/2002 | Wiseman et al. |
| 6,503,257 B2 | 1/2003 | Grant et al. |
| 6,514,283 B2 | 2/2003 | DiMatteo et al. |
| 6,514,534 B1 | 2/2003 | Sawhney |
| 6,517,566 B1 | 2/2003 | Hovland et al. |
| 6,551,356 B2 | 4/2003 | Rousseau |
| 6,566,406 B1 | 5/2003 | Pathak et al. |
| 6,568,398 B2 | 5/2003 | Cohen |
| 6,590,095 B1 | 7/2003 | Schleicher et al. |
| 6,592,597 B2 | 7/2003 | Grant et al. |
| 6,605,294 B2 | 8/2003 | Sawhney |
| 6,610,006 B1 | 8/2003 | Amid et al. |
| 6,627,749 B1 | 9/2003 | Kumar |
| 6,638,285 B2 | 10/2003 | Gabbay |
| 6,652,594 B2 | 11/2003 | Francis et al. |
| 6,656,193 B2 | 12/2003 | Grant et al. |
| 6,656,200 B2 | 12/2003 | Li et al. |
| 6,669,735 B1 | 12/2003 | Pelissier |
| 6,673,093 B1 | 1/2004 | Sawhney |
| 6,677,258 B2 | 1/2004 | Carroll et al. |

(56) References Cited

U.S. PATENT DOCUMENTS

| | | |
|---|---|---|
| 6,685,714 B2 | 2/2004 | Rousseau |
| 6,702,828 B2 | 3/2004 | Whayne |
| 6,703,047 B2 | 3/2004 | Sawhney et al. |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,746,869 B2 | 6/2004 | Pui et al. |
| 6,764,720 B2 | 7/2004 | Pui et al. |
| 6,773,458 B1 | 8/2004 | Brauker et al. |
| 6,818,018 B1 | 11/2004 | Sawhney |
| 6,843,252 B2 | 1/2005 | Harrison et al. |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,953,139 B2 | 10/2005 | Milliman et al. |
| 6,959,851 B2 | 11/2005 | Heinrich |
| 7,009,034 B2 | 3/2006 | Pathak et al. |
| 7,025,772 B2 | 4/2006 | Gellman et al. |
| 7,060,087 B2 | 6/2006 | DiMatteo et al. |
| 7,087,065 B2 | 8/2006 | Ulmsten et al. |
| 7,108,701 B2 | 9/2006 | Evens et al. |
| 7,128,253 B2 | 10/2006 | Mastri et al. |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 | 12/2006 | Shelton, IV |
| 7,160,299 B2 | 1/2007 | Baily |
| 7,179,268 B2 | 2/2007 | Roy et al. |
| 7,210,810 B1 | 5/2007 | Iversen et al. |
| 7,214,727 B2 | 5/2007 | Kwon et al. |
| 7,232,449 B2 | 6/2007 | Sharkawy et al. |
| 7,241,300 B2 | 7/2007 | Sharkawy et al. |
| 7,247,338 B2 | 7/2007 | Pui et al. |
| 7,279,322 B2 | 10/2007 | Pui et al. |
| 7,307,031 B2 | 12/2007 | Carroll et al. |
| 7,308,998 B2 | 12/2007 | Mastri et al. |
| 7,311,720 B2 | 12/2007 | Mueller et al. |
| 7,328,829 B2 | 2/2008 | Arad et al. |
| 7,334,717 B2 | 2/2008 | Rethy et al. |
| 7,347,850 B2 | 3/2008 | Sawhney |
| 7,377,928 B2 | 5/2008 | Zubik et al. |
| 7,434,717 B2 | 10/2008 | Shelton, IV et al. |
| 7,438,209 B1 | 10/2008 | Hess |
| 7,464,849 B2 | 12/2008 | Shelton, IV et al. |
| 7,498,063 B2 | 3/2009 | Pui et al. |
| 7,547,312 B2 | 6/2009 | Bauman et al. |
| 7,559,937 B2 | 7/2009 | de la Torre et al. |
| 7,571,845 B2 | 8/2009 | Viola |
| 7,592,418 B2 | 9/2009 | Pathak et al. |
| 7,594,921 B2 | 9/2009 | Browning |
| 7,595,392 B2 | 9/2009 | Kumar et al. |
| 7,604,151 B2 | 10/2009 | Hess et al. |
| 7,611,494 B2 | 11/2009 | Campbell et al. |
| 7,635,073 B2 | 12/2009 | Heinrich |
| 7,645,874 B2 | 1/2010 | Saferstein et al. |
| 7,649,089 B2 | 1/2010 | Kumar et al. |
| 7,655,288 B2 | 2/2010 | Bauman et al. |
| 7,662,409 B2 | 2/2010 | Masters |
| 7,662,801 B2 | 2/2010 | Kumar et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,673,782 B2 | 3/2010 | Hess et al. |
| 7,708,180 B2 | 5/2010 | Murray et al. |
| 7,709,631 B2 | 5/2010 | Harris et al. |
| 7,717,313 B2 | 5/2010 | Criscuolo et al. |
| 7,722,642 B2 | 5/2010 | Williamson, IV et al. |
| 7,735,703 B2 | 6/2010 | Morgan et al. |
| 7,744,627 B2 | 6/2010 | Orban, III et al. |
| 7,754,002 B2 | 7/2010 | Maase et al. |
| 7,776,060 B2 | 8/2010 | Mooradian et al. |
| 7,789,889 B2 | 9/2010 | Zubik et al. |
| 7,793,813 B2 | 9/2010 | Bettuchi |
| 7,799,026 B2 | 9/2010 | Schechter et al. |
| 7,819,896 B2 | 10/2010 | Racenet |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban, III et al. |
| 7,951,248 B1 | 5/2011 | Fallis et al. |
| 7,967,179 B2 | 6/2011 | Olson et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,177 B2 | 9/2011 | Bettuchi et al. |
| 8,016,178 B2 | 9/2011 | Olson et al. |
| 8,025,199 B2 | 9/2011 | Whitman et al. |
| 8,028,883 B2 | 10/2011 | Stopek |
| 8,033,483 B2 | 10/2011 | Fortier et al. |
| 8,033,983 B2 | 10/2011 | Chu et al. |
| 8,038,045 B2 | 10/2011 | Bettuchi et al. |
| 8,062,330 B2 | 11/2011 | Prommersberger et al. |
| 8,062,673 B2 | 11/2011 | Figuly et al. |
| 8,083,119 B2 | 12/2011 | Prommersberger |
| 8,091,756 B2 | 1/2012 | Viola |
| 8,123,766 B2 | 2/2012 | Bauman et al. |
| 8,123,767 B2 | 2/2012 | Bauman et al. |
| 8,127,975 B2 | 3/2012 | Olson et al. |
| 8,133,336 B2 | 3/2012 | Kettlewell et al. |
| 8,133,559 B2 | 3/2012 | Lee et al. |
| 8,146,791 B2 | 4/2012 | Bettuchi et al. |
| 8,152,777 B2 | 4/2012 | Campbell et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,177,797 B2 | 5/2012 | Shimoji et al. |
| 8,178,746 B2 | 5/2012 | Hildeberg et al. |
| 8,192,460 B2 | 6/2012 | Orban, III et al. |
| 8,201,720 B2 | 6/2012 | Hessler |
| 8,210,414 B2 | 7/2012 | Bettuchi et al. |
| 8,210,453 B2 | 7/2012 | Hull et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,252,339 B2 | 8/2012 | Figuly et al. |
| 8,252,921 B2 | 8/2012 | Vignon et al. |
| 8,256,654 B2 | 9/2012 | Bettuchi et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,317,790 B2 | 11/2012 | Bell et al. |
| 8,322,590 B2 | 12/2012 | Patel et al. |
| 8,348,126 B2 | 1/2013 | Olson et al. |
| 8,348,130 B2 | 1/2013 | Shah et al. |
| 8,365,972 B2 | 2/2013 | Aranyi et al. |
| 8,367,089 B2 | 2/2013 | Wan et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,393,514 B2 | 3/2013 | Shelton, IV et al. |
| 8,393,517 B2 | 3/2013 | Milo |
| 8,408,440 B2 | 4/2013 | Olson et al. |
| 8,408,480 B2 | 4/2013 | Hull et al. |
| 8,413,869 B2 | 4/2013 | Heinrich |

(56) References Cited

U.S. PATENT DOCUMENTS

| | | |
|---|---|---|
| 8,413,871 B2 | 4/2013 | Racenet et al. |
| 8,418,909 B2 | 4/2013 | Kostrzewski |
| 8,424,742 B2 | 4/2013 | Bettuchi |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |
| 8,464,925 B2 | 6/2013 | Hull et al. |
| 8,470,360 B2 | 6/2013 | McKay |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 | 8/2013 | Marczyk et al. |
| 8,518,440 B2 | 8/2013 | Blaskovich et al. |
| 8,529,600 B2 | 9/2013 | Woodard, Jr. et al. |
| 8,540,128 B2 | 9/2013 | Shelton, IV et al. |
| 8,540,131 B2 | 9/2013 | Swayze |
| 8,551,138 B2 | 10/2013 | Orban, III et al. |
| 8,556,918 B2 | 10/2013 | Bauman et al. |
| 8,561,873 B2 | 10/2013 | Ingmanson et al. |
| 8,579,990 B2 | 11/2013 | Priewe |
| 8,584,920 B2 | 11/2013 | Hodgkinson |
| 8,590,762 B2 | 11/2013 | Hess et al. |
| 8,616,430 B2 | 12/2013 | (Prommersberger) Stopek et al. |
| 8,617,132 B2 | 12/2013 | Golzarian et al. |
| 8,631,989 B2 | 1/2014 | Aranyi et al. |
| 8,646,674 B2 | 2/2014 | Schulte et al. |
| 8,668,129 B2 | 3/2014 | Olson |
| 8,678,263 B2 | 3/2014 | Viola |
| 8,679,137 B2 | 3/2014 | Bauman et al. |
| 8,684,250 B2 | 4/2014 | Bettuchi et al. |
| 8,701,958 B2 | 4/2014 | Shelton, IV et al. |
| 8,721,703 B2 | 5/2014 | Fowler |
| 8,727,197 B2 | 5/2014 | Hess et al. |
| 8,757,466 B2 | 6/2014 | Olson et al. |
| 8,789,737 B2 | 7/2014 | Hodgkinson et al. |
| 8,814,888 B2 | 8/2014 | Sgro |
| 8,820,606 B2 | 9/2014 | Hodgkinson |
| 8,827,133 B2 | 9/2014 | Shelton, IV et al. |
| 8,857,694 B2 | 10/2014 | Shelton, IV et al. |
| 8,864,009 B2 | 10/2014 | Shelton, IV et al. |
| 8,870,050 B2 | 10/2014 | Hodgkinson |
| 8,920,443 B2 | 12/2014 | Hiles et al. |
| 8,920,444 B2 | 12/2014 | Hiles et al. |
| 8,939,344 B2 | 1/2015 | Olson et al. |
| 8,956,390 B2 | 2/2015 | Shah et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | (Prommersberger) Stopek et al. |
| 9,016,544 B2 | 4/2015 | Hodgkinson et al. |
| 9,027,817 B2 | 5/2015 | Milliman et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,871 B2 | 8/2015 | Milliman et al. |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 9,186,140 B2 | 11/2015 | Hiles et al. |
| 9,186,144 B2 | 11/2015 | Stevenson et al. |
| 9,192,378 B2 | 11/2015 | Aranyi et al. |
| 9,192,379 B2 | 11/2015 | Aranyi et al. |
| 9,192,380 B2 | 11/2015 | (Tarinelli) Racenet et al. |
| 9,192,383 B2 | 11/2015 | Milliman |
| 9,192,384 B2 | 11/2015 | Bettuchi |
| 9,198,660 B2 | 12/2015 | Hodgkinson |
| 9,198,663 B1 | 12/2015 | Marczyk et al. |
| 9,204,881 B2 | 12/2015 | Penna |
| 9,220,504 B2 | 12/2015 | Viola et al. |
| 9,226,754 B2 | 1/2016 | D'Agostino et al. |
| 9,237,892 B2 | 1/2016 | Hodgkinson |
| 9,237,893 B2 | 1/2016 | Carter et al. |
| 9,277,922 B2 | 3/2016 | Carter et al. |
| 9,295,466 B2 | 3/2016 | Hodgkinson et al. |
| 9,326,768 B2 | 5/2016 | Shelton, IV |
| 9,326,773 B2 | 5/2016 | Casasanta, Jr. et al. |
| 9,328,111 B2 | 5/2016 | Zhou |
| 9,345,479 B2 | 5/2016 | (Tarinelli) Racenet et al. |
| 9,351,729 B2 | 5/2016 | Orban, III et al. |
| 9,351,731 B2 | 5/2016 | Carter et al. |
| 9,351,732 B2 | 5/2016 | Hodgkinson |
| 9,358,005 B2 | 6/2016 | Shelton, IV et al. |
| 9,364,229 B2 | 6/2016 | D'Agostino et al. |
| 9,364,234 B2 | 6/2016 | (Prommersberger) Stopek et al. |
| 9,386,988 B2 | 7/2016 | Baxter, III et al. |
| 9,402,627 B2 | 8/2016 | Stevenson et al. |
| 9,414,839 B2 | 8/2016 | Penna |
| 9,433,412 B2 | 9/2016 | Bettuchi et al. |
| 9,433,413 B2 | 9/2016 | Stopek |
| 9,433,420 B2 | 9/2016 | Hodgkinson |
| 9,445,812 B2 | 9/2016 | Olson et al. |
| 9,445,817 B2 | 9/2016 | Bettuchi |
| 9,463,260 B2 | 10/2016 | Stopek |
| 9,486,215 B2 | 11/2016 | Olson et al. |
| 9,492,170 B2 | 11/2016 | Bear et al. |
| 9,504,470 B2 | 11/2016 | Milliman |
| 9,517,164 B2 | 12/2016 | Vitaris et al. |
| 9,572,576 B2 | 2/2017 | Hodgkinson et al. |
| 9,585,657 B2 | 3/2017 | Shelton, IV et al. |
| 9,597,077 B2 | 3/2017 | Hodgkinson |
| 9,610,080 B2 | 4/2017 | Whitfield et al. |
| 9,622,745 B2 | 4/2017 | Ingmanson et al. |
| 9,629,626 B2 | 4/2017 | Soltz et al. |
| 9,636,850 B2 | 5/2017 | Stopek et al. |
| 9,655,620 B2 | 5/2017 | Prescott et al. |
| 9,675,351 B2 | 6/2017 | Hodgkinson et al. |
| 9,681,936 B2 | 6/2017 | Hodgkinson et al. |
| 9,687,262 B2 | 6/2017 | Rousseau et al. |
| 9,693,772 B2 | 7/2017 | Ingmanson et al. |
| 9,708,184 B2 | 7/2017 | Chan et al. |
| 9,770,245 B2 | 9/2017 | Swayze et al. |
| 9,775,617 B2 | 10/2017 | Carter et al. |
| 9,775,618 B2 | 10/2017 | Bettuchi et al. |
| 9,782,173 B2 | 10/2017 | Mozdzierz |
| 9,844,378 B2 | 12/2017 | Casasanta et al. |
| 9,918,713 B2 | 3/2018 | Zergiebel et al. |
| 9,931,116 B2 | 4/2018 | Racenet et al. |
| 10,022,125 B2 | 7/2018 | (Prommersberger) Stopek et al. |
| 2002/0091397 A1 | 7/2002 | Chen |
| 2002/0151911 A1 | 10/2002 | Gabbay |
| 2003/0065345 A1 | 4/2003 | Weadock |
| 2003/0078209 A1 | 4/2003 | Schmidt |
| 2003/0083676 A1 | 5/2003 | Wallace |
| 2003/0125676 A1 | 7/2003 | Swenson et al. |
| 2003/0181927 A1 | 9/2003 | Wallace |
| 2003/0208231 A1 | 11/2003 | Williamson et al. |
| 2004/0092912 A1 | 5/2004 | Jinno et al. |
| 2004/0107006 A1 | 6/2004 | Francis et al. |
| 2004/0131418 A1 | 7/2004 | Budde et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0006429 A1 | 1/2005 | Wales et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0149073 A1 | 7/2005 | Arani et al. |
| 2005/0283256 A1 | 12/2005 | Sommerich et al. |
| 2006/0008505 A1 | 1/2006 | Brandon |
| 2006/0025816 A1 | 2/2006 | Shelton |
| 2006/0121266 A1 | 6/2006 | Fandel et al. |

(56) References Cited

U.S. PATENT DOCUMENTS

| | | |
|---|---|---|
| 2006/0173470 A1 | 8/2006 | Oray et al. |
| 2006/0190027 A1 | 8/2006 | Downey |
| 2007/0034669 A1 | 2/2007 | de la Torre et al. |
| 2007/0203510 A1 | 8/2007 | Bettuchi |
| 2007/0243227 A1 | 10/2007 | Gertner |
| 2007/0246505 A1* | 10/2007 | Pace-Floridia ....... A61L 31/044 227/175.1 |
| 2008/0009811 A1 | 1/2008 | Cantor |
| 2008/0029570 A1 | 2/2008 | Shelton et al. |
| 2008/0082126 A1 | 4/2008 | Murray et al. |
| 2008/0140115 A1 | 6/2008 | Stopek |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0216855 A1 | 9/2008 | Nasca |
| 2008/0220047 A1 | 9/2008 | Sawhney et al. |
| 2008/0290134 A1 | 11/2008 | Bettuchi et al. |
| 2008/0314960 A1 | 12/2008 | Marczyk et al. |
| 2009/0001121 A1 | 1/2009 | Hess et al. |
| 2009/0001122 A1* | 1/2009 | Prommersberger .... B29C 39/22 227/176.1 |
| 2009/0001130 A1 | 1/2009 | Hess et al. |
| 2009/0031842 A1 | 2/2009 | Kawai et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0218384 A1 | 9/2009 | Aranyi |
| 2009/0277944 A9 | 11/2009 | Dalessandro et al. |
| 2010/0016855 A1 | 1/2010 | Ramstein et al. |
| 2010/0016888 A1 | 1/2010 | Calabrese et al. |
| 2010/0087840 A1 | 4/2010 | Ebersole et al. |
| 2010/0147921 A1 | 6/2010 | Olson |
| 2010/0147922 A1 | 6/2010 | Olson |
| 2010/0174253 A1 | 7/2010 | Cline et al. |
| 2010/0203151 A1 | 8/2010 | Hiraoka |
| 2010/0243707 A1 | 9/2010 | Olson et al. |
| 2010/0243711 A1* | 9/2010 | Olson ................ A61B 17/0682 227/181.1 |
| 2010/0314502 A1* | 12/2010 | Miles ........................ F16L 3/14 248/59 |
| 2010/0331859 A1 | 12/2010 | Omori |
| 2011/0017213 A1* | 1/2011 | Vadney .................. A61B 50/10 128/204.17 |
| 2011/0034910 A1 | 2/2011 | Ross et al. |
| 2011/0087279 A1 | 4/2011 | Shah et al. |
| 2011/0089220 A1 | 4/2011 | Ingmanson et al. |
| 2011/0118761 A1* | 5/2011 | Baxter, III ........... A61B 17/115 606/148 |
| 2011/0125138 A1 | 5/2011 | Malinouskas et al. |
| 2011/0152900 A1* | 6/2011 | Regadas ............. A61B 17/1114 606/153 |
| 2011/0166673 A1 | 7/2011 | Patel et al. |
| 2011/0251639 A1 | 10/2011 | Thomas et al. |
| 2011/0293690 A1 | 12/2011 | Griffin et al. |
| 2012/0080336 A1 | 4/2012 | Shelton, IV et al. |
| 2012/0145767 A1 | 6/2012 | Shah et al. |
| 2012/0150206 A1* | 6/2012 | Barikosky ........... A61B 17/115 606/153 |
| 2012/0197272 A1 | 8/2012 | Oray et al. |
| 2012/0234899 A1* | 9/2012 | Scheib ............. A61B 17/12013 227/180.1 |
| 2012/0241491 A1 | 9/2012 | Aldridge et al. |
| 2012/0241493 A1 | 9/2012 | Baxter, III et al. |
| 2012/0241503 A1 | 9/2012 | Baxter, III et al. |
| 2012/0253298 A1 | 10/2012 | Henderson et al. |
| 2012/0273547 A1* | 11/2012 | Hodgkinson ..... A61B 17/07292 227/176.1 |
| 2013/0105548 A1 | 5/2013 | Hodgkinson et al. |
| 2013/0153634 A1* | 6/2013 | Carter ................ A61B 17/1155 227/176.1 |
| 2013/0153636 A1 | 6/2013 | Shelton, IV et al. |
| 2013/0153641 A1 | 6/2013 | Shelton, IV et al. |
| 2013/0193190 A1* | 8/2013 | Carter .............. A61B 17/07292 227/179.1 |
| 2013/0256380 A1 | 10/2013 | Schmid et al. |
| 2014/0048580 A1 | 2/2014 | Merchant et al. |
| 2014/0131418 A1* | 5/2014 | Kostrzewski ........ A61B 17/068 227/176.1 |
| 2014/0138423 A1 | 5/2014 | Whitfield et al. |
| 2014/0239047 A1 | 8/2014 | Hodgkinson et al. |
| 2015/0041347 A1 | 2/2015 | Hodgkinson |
| 2015/0133995 A1 | 5/2015 | Shelton, IV et al. |
| 2015/0157320 A1 | 6/2015 | Zergiebel et al. |
| 2015/0157321 A1 | 6/2015 | Zergiebel et al. |
| 2015/0209045 A1 | 7/2015 | Hodgkinson et al. |
| 2015/0231409 A1 | 8/2015 | Racenet et al. |
| 2015/0327864 A1 | 11/2015 | Hodgkinson et al. |
| 2015/0351761 A1* | 12/2015 | Shelton, IV ..... A61B 17/07292 606/219 |
| 2016/0015382 A1* | 1/2016 | Alexander ....... A61B 17/06109 606/139 |
| 2016/0022268 A1 | 1/2016 | Prior |
| 2016/0045200 A1 | 2/2016 | Milliman |
| 2016/0100834 A1 | 4/2016 | Viola et al. |
| 2016/0106430 A1 | 4/2016 | Carter et al. |
| 2016/0157857 A1 | 6/2016 | Hodgkinson et al. |
| 2016/0174988 A1 | 6/2016 | D'Agostino et al. |
| 2016/0206315 A1 | 7/2016 | Olson |
| 2016/0220257 A1 | 8/2016 | Casasanta et al. |
| 2016/0249923 A1 | 9/2016 | Hodgkinson et al. |
| 2016/0270793 A1 | 9/2016 | Carter et al. |
| 2016/0310143 A1 | 10/2016 | Bettuchi |
| 2016/0338704 A1 | 11/2016 | Penna |
| 2016/0367252 A1 | 12/2016 | Olson et al. |
| 2016/0367253 A1 | 12/2016 | Hodgkinson |
| 2016/0367257 A1 | 12/2016 | Stevenson et al. |
| 2017/0042540 A1 | 2/2017 | Olson et al. |
| 2017/0049452 A1 | 2/2017 | Milliman |
| 2017/0056017 A1 | 3/2017 | Vendely et al. |
| 2017/0086825 A1* | 3/2017 | Henderson ....... A61B 17/06166 |
| 2017/0086847 A1* | 3/2017 | DiNardo ............. A61B 17/105 |
| 2017/0119385 A1 | 5/2017 | Shelton, IV et al. |
| 2017/0150967 A1 | 6/2017 | Hodgkinson et al. |
| 2017/0172575 A1 | 6/2017 | Hodgkinson |
| 2017/0231629 A1 | 8/2017 | Stopek et al. |
| 2017/0238931 A1 | 8/2017 | Prescott et al. |
| 2017/0281328 A1 | 10/2017 | Hodgkinson et al. |
| 2017/0296188 A1 | 10/2017 | Ingmanson et al. |
| 2017/0354415 A1 | 12/2017 | Casasanta, Jr. et al. |
| 2018/0125491 A1 | 5/2018 | Aranyi |
| 2018/0140301 A1 | 5/2018 | Milliman |
| 2018/0168654 A1 | 6/2018 | Hodgkinson et al. |
| 2018/0214147 A1 | 8/2018 | Merchant et al. |
| 2018/0235626 A1* | 8/2018 | Shelton, IV ..... A61B 17/07207 |
| 2019/0125346 A1 | 5/2019 | Zhao et al. |

FOREIGN PATENT DOCUMENTS

| | | |
|---|---|---|
| DE | 19924311 A1 | 11/2000 |
| EP | 0327022 A2 | 8/1989 |
| EP | 0594148 A1 | 4/1994 |
| EP | 2491867 A1 | 8/2012 |
| JP | 2000166933 A | 6/2000 |
| JP | 2002202213 A | 7/2002 |
| JP | 2007124166 A | 5/2007 |
| JP | 2010214132 A | 9/2010 |
| WO | 9005489 A1 | 5/1990 |
| WO | 95/16221 A1 | 6/1995 |
| WO | 98/38923 A1 | 9/1998 |
| WO | 9926826 A2 | 6/1999 |
| WO | 0010456 A1 | 3/2000 |
| WO | 0016684 A1 | 3/2000 |
| WO | 2010075298 A2 | 7/2010 |

OTHER PUBLICATIONS

Australian Examination Report No. 1 corresponding to AU 2014200793 dated Sep. 2, 2017.

Extended European Search Report corresponding to EP 17 17 8528.0 dated Oct. 13, 2017.

(56) References Cited

OTHER PUBLICATIONS

Australian Examination Report No. 1 corresponding to AU 2013234420 dated Oct. 24, 2017.
Japanese Office Action corresponding to JP 2013-175379 dated Oct. 20, 2017.
Japanese Office Action corresponding to JP 2013-147701 dated Oct. 27, 2017.
Extended European Search Report corresponding to EP 17 17 5656.2 dated Nov. 7, 2017.
Japanese Office Action corresponding to JP 2014-009738 dated Nov. 14, 2017.
European Office Action corresponding to EP 13 17 3986.4 dated Nov. 29, 2017.
Japanese Office Action corresponding to JP 2017-075975 dated Dec. 4, 2017.
European Office Action corresponding to EP 13 19 7958.5 dated Dec. 11, 2017.
Chinese First Office Action corresponding to Patent Application CN 201410588811.8 dated Dec. 5, 2017.
European Office Action corresponding to Patent Application EP 16 16 6367.9 dated Dec. 11, 2017.
Chinese First Office Action corresponding to Patent Application CN 201610279682.3 dated Jan. 10, 2018.
Japanese Office Action corresponding to Patent Application JP 2013-154561 dated Jan. 15, 2018.
Australian Examination Report No. 1 corresponding to Patent Application AU 2017225037 dated Jan. 23, 2018.
Japanese Office Action corresponding to Patent Application JP 2013-229471 dated May 1, 2018.
Canadian Office Action corresponding to Patent Application CA 2,790,743 dated May 14, 2018.
European Office Action corresponding to Patent Application EP 14 15 7195.0 dated Jun. 12, 2018.
European Search Report corresponding to EP 06 00 4598, completed Jun. 22, 2006; (2 pp).
European Search Report corresponding to EP 06 01 6962.0, completed Jan. 3, 2007 and dated Jan. 11, 2007; (10 pp).
International Search Report corresponding to International Application No. PCT/US2005/036740, completed Feb. 20, 2007 and dated Mar. 23, 2007; (8 pp).
International Search Report corresponding to International Application No. PCT/US2007/022713, completed Apr. 21, 2008 and dated May 15, 2008; (1 p).
International Search Report corresponding to International Application No. PCT/US2008/002981, completed Jun. 9, 2008 and dated Jun. 26, 2008; (2 pp).
European Search Report corresponding to EP 08 25 1779, completed Jul. 14, 2008 and dated Jul. 23, 2008; (5 pp).
European Search Report corresponding to EP 08 25 1989.3, completed Mar. 11, 2010 and dated Mar. 24, 2010; (6 pp).
European Search Report corresponding to EP 10 25 0639.1, completed Jun. 17, 2010 and dated Jun. 28, 2010; (7 pp).
European Search Report corresponding to EP 10 25 0715.9, completed Jun. 30, 2010 and dated Jul. 20, 2010; (3 pp).
European Search Report corresponding to EP 05 80 4382.9, completed Oct. 5, 2010 and dated Oct. 12, 2010; (3 pp).
European Search Report corresponding to EP 09 25 2897.5, completed Feb. 7, 2011 and dated Feb. 15, 2011; (3 pp).
European Search Report corresponding to EP 10 25 0642.5, completed Mar. 25, 2011 and dated Apr. 4, 2011; (4 pp).
European Search Report corresponding to EP 12 15 2229.6, completed Feb. 23, 2012 and dated Mar. 1, 2012; (4 pp).
European Search Report corresponding to EP 12 15 0511.9, completed Apr. 16, 2012 and dated Apr. 24, 2012; (7 pp).
European Search Report corresponding to EP 12 15 2541.4, completed Apr. 23, 2012 and dated May 3, 2012; (10 pp).
European Search Report corresponding to EP 12 16 5609.4, completed Jul. 5, 2012 and dated Jul. 13, 2012; (8 pp).
European Search Report corresponding to EP 12 15 8861.0, completed Jul. 17, 2012 and dated Jul. 24, 2012; (9 pp).
European Search Report corresponding to EP 12 16 5878.5, completed Jul. 24, 2012 and dated Aug. 6, 2012; (8 pp).
Extended European Search Report corresponding to EP 12 19 1035.0, completed Jan. 11, 2013 and dated Jan. 18, 2013; (7 pp).
Extended European Search Report corresponding to EP 12 18 6175.1, completed Jan. 15, 2013 and dated Jan. 23, 2013; (7 pp).
Extended European Search Report corresponding to EP 12 19 1114.3, completed Jan. 23, 2013 and dated Jan. 31, 2013; (10 pp).
Extended European Search Report corresponding to EP 12 19 2224.9, completed Mar. 14, 2013 and dated Mar. 26, 2013; (8 pp).
Extended European Search Report corresponding to EP 12 19 6904.2, completed Mar. 28, 2013 and dated Jul. 26, 2013; (8 pp).
Extended European Search Report corresponding to EP 12 19 6911.7, completed Apr. 18, 2013 and dated Apr. 24, 2013; (8 pp).
Extended European Search Report corresponding to EP 07 00 5842.5, completed May 13, 2013 and dated May 29, 2013; (7 pp).
Extended European Search Report corresponding to EP 12 19 8776.2, completed May 16, 2013 and dated May 27, 2013; (8 pp).
Extended European Search Report corresponding to EP 12 19 8749.9, completed May 21, 2013 and dated May 31, 2013; (8 pp).
Extended European Search Report corresponding to EP 13 15 6297.7, completed Jun. 4, 2013 and dated Jun. 13, 2013; (7 pp).
Extended European Search Report corresponding to EP 13 17 3985.6, completed Aug. 19, 2013 and dated Aug. 28, 2013; (6 pp).
Extended European Search Report corresponding to EP 13 17 3986.4, completed Aug. 20, 2013 and dated Aug. 29, 2013; (6 pp).
Extended European Search Report corresponding to EP 13 17 7437.4, completed Sep. 11, 2013 and dated Sep. 19, 2013; 6 pages.
Extended European Search Report corresponding to EP 13 17 7441.6, completed Sep. 11, 2013 and dated Sep. 19, 2013; (6 pp).
Extended European Search Report corresponding to EP 07 86 1534.1, completed Sep. 20, 2013 and dated Sep. 30, 2013; (5 pp).
Extended European Search Report corresponding to EP 13 18 3876.5, completed Oct. 14, 2013 and dated Oct. 24, 2013; (5 pp).
Extended European Search Report corresponding to EP 13 17 1856.1, completed Oct. 29, 2013 and dated Nov. 7, 2013; (8 pp).
Extended European Search Report corresponding to EP 13 18 0373.6, completed Oct. 31, 2013 and dated Nov. 13, 2013; (7 pp).
Extended European Search Report corresponding to EP 13 18 0881.8, completed Nov. 5, 2013 and dated Nov. 14, 2013; (6 pp).
Extended European Search Report corresponding to EP 13 17 6895.4, completed Nov. 29, 2013 and dated Dec. 12, 2013; (5 pp).
Extended European Search Report corresponding to EP 13 18 2911.1, completed Dec. 2, 2013 and dated Dec. 16, 2013; (8 pp).
Extended European Search Report corresponding to EP 10 25 1795.0, completed Dec. 11, 2013 and dated Dec. 20, 2013; (6 pp).
Extended European Search Report corresponding to EP 13 18 7911.6, completed Jan. 22, 2014 and dated Jan. 31, 2014; (8 pp).
Extended European Search Report corresponding to EP 13 19 2111.6, completed Feb. 13, 2014 and dated Feb. 27, 2014; (10 pp).
Extended European Search Report corresponding to EP 13 19 5919.9, completed Feb. 10, 2014 and dated -Mar. 3, 2014; (7 pp).
Extended European Search Report corresponding to EP 08 72 6500.5, completed Feb. 20, 2014 and dated Mar. 3, 2014; (7 pp).
Extended European Search Report corresponding to EP 13 19 5019.8, completed Mar. 14, 2014 and dated Mar. 4, 2014; (7 pp).
Extended European Search Report corresponding to EP 13 19 6816.6, completed Mar. 28, 2014 and dated Apr. 9, 2014; (9 pp).
Extended European Search Report corresponding to EP 13 19 7958.5, completed Apr. 4, 2014 and dated Apr. 15, 2014; (8 pp).
Extended European Search Report corresponding to EP 13 19 4995.0, completed Jun. 5, 2014 and dated Jun. 16, 2014; (5 pp).
Extended European Search Report corresponding to EP 14 15 7195.0, completed Jun. 5, 2014 and dated Jun. 18, 2014; (9 pp).
Extended European Search Report corresponding to EP 14 15 6342.9, completed Jul. 22, 2014 and dated Jul. 29, 2014; (8 pp).
European Office Action corresponding to EP 14 17 2681.0 dated May 13, 2016.
Extended European Search Report corresponding to EP 16 15 3647.9 dated Jun. 3, 2016.
Chinese Office Action corresponding to CN 201210545228 dated Jun. 29, 2016.

(56) References Cited

OTHER PUBLICATIONS

Japanese Office Action corresponding to JP 2012-250058 dated Jun. 29, 2016.
European Office Action corresponding to EP 14 15 7997.9 dated Jun. 29, 2016.
Canadian Office Action corresponding to CA 2,712,617 dated Jun. 30, 2016.
Chinese First Office Action corresponding to CN 2013103036903 dated Jun. 30, 2016.
Australian Patent Examination Report No. 1 corresponding to AU 2012250278 dated Jul. 10, 2016.
Australian Patent Examination Report No. 1 corresponding to AU 2012244382 dated Jul. 10, 2016.
Japanese Office Action corresponding to 2012-255242 dated Jul. 26, 2016.
Japanese Office Action corresponding to JP 2012-268668 dated Jul. 27, 2016.
European Office Action corresponding to EP 14 15 2060.1 dated Aug. 4, 2016.
European Office Action corresponding to EP 12 16 5609.4 dated Aug. 5, 2016.
European Office Action corresponding to EP 15 15 2392.5 dated Aug. 8, 2016.
Japanese Office Action corresponding to JP 2013-003624 dated Aug. 25, 2016.
Australian Patent Examination Report No. 1 corresponding to AU 2012261752 dated Sep. 6, 2016.
Japanese Office Action corresponding to JP 2014-252703 dated Sep. 26, 2016.
European Office Action corresponding to EP 12 19 8776.2 dated Sep. 12, 2016.
Japanese Office Action corresponding to JP 2013-000321 dated Sep. 13, 2016.
Chinese Second Office Action corresponding to CN 201310353628.5 dated Sep. 26, 2016.
European Office Action corresponding to EP 12 15 2541.4 dated Sep. 27, 2016.
Australian Patent Examination Report No. 1 corresponding to AU 2012268923 dated Sep. 28, 2016.
Chinese First Office Action corresponding to CN 2013107068710 dated Dec. 16, 2016.
Chinese First Office Action corresponding to CN 201310646606.8 dated Dec. 23, 2016.
Japanese Office Action corresponding to JP 2013-000321 dated Jan. 4, 2017.
Extended European Search Report corresponding to EP 16 16 6367.9 dated Jan. 16, 2017.
Australian Examination Report No. 1 corresponding to AU 2013206777 dated Feb. 1, 2017.
Chinese Second Office Action corresponding to CN 2013103036903 dated Feb. 23, 2017.
Japanese Office Action corresponding to JP 2013-175379 dated Mar. 1, 2017.
Chinese First Office Action corresponding to CN 201410028462.4 dated Mar. 2, 2017.
Chinese First Office Action corresponding to CN 201410084070 dated Mar. 13, 2017.
Extended European Search Report corresponding to EP 16 19 6549.6 dated Mar. 17, 2017.
Japanese Office Action corresponding to JP 2013-147701 dated Mar. 21, 2017.
Australian Examination Report No. 1 corresponding to AU 2013206804 dated Mar. 21, 2017.
Australian Examination Report No. 1 corresponding to AU 2013211499 dated May 4, 2017.
Australian Examination Report No. 1 corresponding to AU 2014201008 dated May 23, 2017.
European Office Action corresponding to EP 15 17 4146.9 dated May 15, 2017.
Japanese Office Action corresponding to JP 2013-154561 dated May 23, 2017.
European Office Action corresponding to EP 12 19 4784.0 dated May 29, 2017.
Japanese Office Action corresponding to JP 2013-169083 dated May 31, 2017.
Australian Examination Report No. 1 corresponding to AU 2013213767 dated Jun. 29, 2017.
Australian Examination Report No. 2 corresponding to AU 2012261752 dated Jul. 7, 2017.
Australian Examination Report No. 1 corresponding to AU 2013266989 dated Jul. 10, 2017.
Extended European Search Report corresponding to EP 14 15 3609.4 dated Jul. 14, 2017.
Australian Examination Report No. 1 corresponding to AU 2013234418 dated Jul. 14, 2017.
Extended European Search Report corresponding to EP 14 15 3610.2 dated Jul. 17, 2017.
Australian Examination Report No. 1 corresponding to AU 2014200109 dated Jul. 20, 2017.
Australian Examination Report No. 1 corresponding to AU 2014200074 dated Jul. 20, 2017.
Japanese Office Action corresponding to JP 2013-250857 dated Aug. 17, 2017.
Japanese Office Action corresponding to JP 2013-229471 dated Aug. 17, 2017.
Extended European Search Report corresponding to EP 14 16 9739.1, completed Aug. 19, 2014 and dated Aug. 29, 2014; (7 pp).
Extended European Search Report corresponding to EP 14 15 7997.9, completed Sep. 9, 2014 and dated Sep. 17, 2014; (8 pp).
Extended European Search Report corresponding to EP 14 16 8904.2, completed Sep. 10, 2014 and dated Sep. 18, 2014; (8 pp).
Extended European Search Report corresponding to EP 13 19 4995.0, completed Jun. 5, 2014 and dated Oct. 13, 2014; (10 pp).
Extended European Search Report corresponding to EP 13 15 4571.7, completed Oct. 10, 2014 and dated Oct. 20, 2014; (8 pp).
Extended European Search Report corresponding to EP 14 18 1125.7, completed Oct. 16, 2014 and dated Oct. 24, 2014; (7 pp).
Extended European Search Report corresponding to EP 14 18 1127.3, completed Oct. 16, 2014 and dated Nov. 10, 2014; (8 pp).
Extended European Search Report corresponding to EP 14 19 0419.3, completed Mar. 24, 2015 and dated Mar. 30, 2015; (6 pp).
European Office Action corresponding to EP 12 198 776.2 dated Apr. 7, 2015.
European Office Action corresponding to EP 13 156 297.7 dated Apr. 10, 2015.
Australian Examination Report No. 1 corresponding to AU 2011250822 dated May 18, 2015.
European Office Action corresponding to EP 12 186 175.1 dated Jun. 1, 2015.
Chinese Office Action corresponding to CN 201010517292.8 dated Jun. 2, 2015.
Extended European Search Report corresponding to EP 14 17 4814.5 dated Jun. 9, 2015.
Australian Examination Report No. 1 corresponding to AU 2014200584 dated Jun. 15, 2015.
European Office Action corresponding to EP 13 180 881.8 dated Jun. 19, 2015.
European Office Action corresponding to EP 14 157 195.0 dated Jul. 2, 2015.
Extended European Search Report corresponding to EP 12 19 6902.6 dated Aug. 6, 2015.
Extended European Search Report corresponding to EP 14 15 2060.1 dated Aug. 14, 2015.
Chinese Office Action corresponding to CN 201210129787.2 dated Aug. 24, 2015.
Canadian Office Action corresponding to CA 2,665,206 dated Nov. 19, 2013.
Chinese Notification of Reexamination corresponding to CN 201010517292.8 dated Jun. 2, 2015.
Japanese Office Action corresponding to JP 2014-216989 dated Sep. 11, 2015.

(56) References Cited

OTHER PUBLICATIONS

Canadian First Office Action corresponding to CA 2,686,105 dated Sep. 17, 2015.
Japanese Office Action corresponding to JP 2012-040188 dated Oct. 21, 2015.
European Communication corresponding to EP 13 17 6895.4 dated Nov. 5, 2015.
Chinese First Office Action corresponding to CN 201210544552 dated Nov. 23, 2015.
Chinese First Office Action corresponding to CN 201210545228 dated Nov. 30, 2015.
Extended European Search Report corresponding to EP 15 18 0491.1 dated Dec. 9, 2015.
Extended European Search Report corresponding to EP 15 18 3819.0 dated Dec. 11, 2015.
Canadian Office Action corresponding to CA 2,697,819 dated Jan. 6, 2016.
Canadian Office Action corresponding to CA 2,696,419 dated Jan. 14, 2016.
European Office Action corresponding to EP 12 19 8776.2 dated Jan. 19, 2016.
Extended European Search Report corresponding to EP 15 17 4146.9 dated Jan. 20, 2016.
Chinese First Office Action corresponding to CN 201310353628.5 dated Jan. 25, 2016.
Extended European Search Report corresponding to EP 12 19 6912.5 dated Feb. 1, 2016.
Japanese Office Action corresponding to JP 2012-098903 dated Feb. 22, 2016.
Extended European Search Report corresponding to EP 12 19 8753.1 dated Feb. 24, 2016.
Chinese First Office Action corresponding to CN 201410449019.4 dated Mar. 30, 2016.
Extended European Search Report corresponding to EP 16 15 0232.3 dated Apr. 12, 2016.
European Office Action corresponding to EP 11 18 3256.4 dated Apr. 20, 2016.
Australian Examination Report No. 1 corresponding to AU 2012244169 dated May 10, 2016.
European Office Action corresponding to EP 10 25 0715.9 dated May 12, 2016.
Chinese First Office Action corresponding to CN 201410778512.0 dated May 13, 2016.
Australian Examination Report No. 1 corresponding to AU 2012227358 dated May 16, 2016.
Japanese Office Action corresponding to JP 2012-040188 dated May 17, 2016.
Australian Examination Report No. 1 corresponding to AU 2012244380 dated May 20, 2016.
Australian Examination Report No. 1 corresponding to AU 2014227480 dated May 21, 2016.
Australian Examination Report No. 1 corresponding to AU 2012254977 dated May 30, 2016.
Extended European Search Report dated Sep. 16, 2019 corresponding to counterpart Patent Application EP 19158469.7.

\* cited by examiner

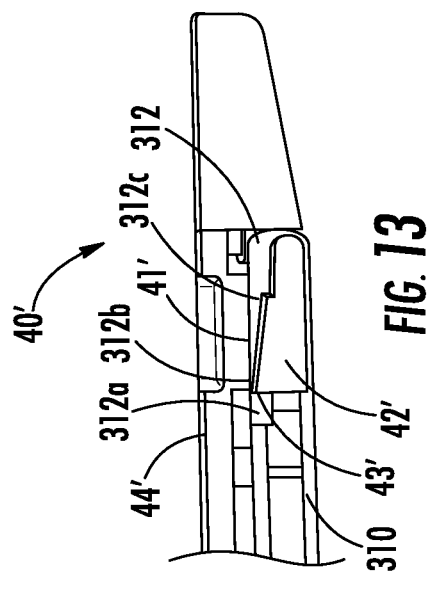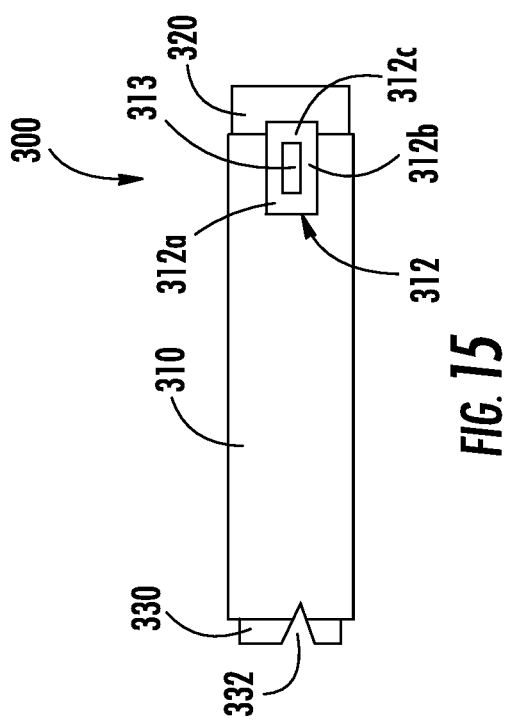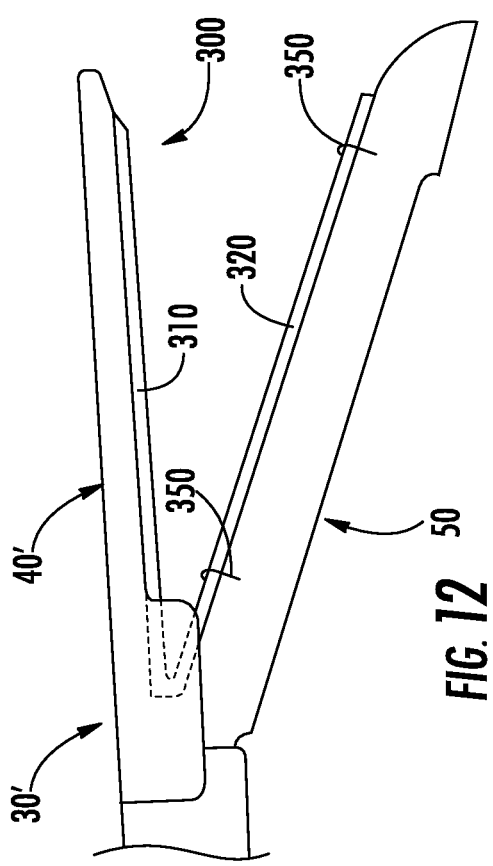

SURGICAL BUTTRESSES FOR SURGICAL STAPLING APPARATUS

CROSS-REFERENCE TO RELATED APPLICATIONS

This application claims the benefit of and priority to U.S. Provisional Patent Application No. 62/633,747 filed Feb. 22, 2018, the entire disclosure of which is incorporated by reference herein.

BACKGROUND

Technical Field

The present disclosure relates to surgical buttresses for use with surgical stapling apparatus, and more particularly, to surgical buttresses that are releasably attached to the surgical stapling apparatus.

Background of Related Art

Surgical stapling apparatus are employed by surgeons to sequentially or simultaneously apply one or more rows of fasteners, e.g., staples or two-part fasteners, to body tissue for the purpose of joining segments of body tissue together. Such apparatus generally include a pair of jaws or finger-like structures between which the body tissue to be joined is placed. When the surgical stapling apparatus is actuated, or "fired", longitudinally moving firing bars contact staple drive members in one of the jaws. The staple drive members push the surgical staples through the body tissue and into an anvil in the opposite jaw which forms the staples. If body tissue is to be removed or separated, a knife blade can be provided in the jaws of the apparatus to cut the body tissue between the lines of staples.

Surgical supports, e.g., meshes or buttress materials, may be used in combination with surgical stapling apparatus to bridge, repair, and/or reinforce tissue defects within a patient such as those occurring, for example, in the abdominal wall, chest wall, diaphragm, or musculo-aponeurotic areas of the body. The buttress material reinforces the staple or suture line as well as covers the juncture of the tissues to reduce leakage prior to healing.

SUMMARY

According to an aspect of the present disclosure, a surgical stapling apparatus includes an end effector having an anvil assembly and a staple cartridge assembly, and an anvil buttress retention system releasably disposed on the anvil assembly. The anvil buttress retention system includes an anvil buttress and a retention member including an elongated body looped around at least a portion of the anvil buttress with a free end of the elongated body extendable through a looped end of the elongated body in an untightened configuration such that the anvil buttress retention system is slidable relative to the anvil assembly. The free end of the retention member is movable relative to and through the looped end to a tightened configuration to secure the anvil buttress retention system to the anvil assembly.

The retention member may include a plurality of barbs extending from the elongated body. The retention member may extend across a central longitudinal slot of the anvil assembly. The retention member may be a first retention member, and the anvil buttress retention assembly may further include a second retention member disposed in spaced relation relative to the first retention member along a length of the anvil buttress.

In embodiments, the anvil buttress is a sleeve defining a cavity therein that is configured to receive the anvil assembly. In some embodiments, the sleeve includes a first layer positionable adjacent a tissue facing surface of the anvil assembly and a second layer positionable adjacent an outwardly facing surface of the anvil assembly. In certain embodiments, the sleeve includes perforations extending along a length thereof and positioned between the first and second layers.

In embodiments, the anvil buttress includes a central portion and a pair of wings extending from the central portion to define a u-shaped channel configured to receive the anvil assembly therein. In some embodiments, the retention member is looped through side edges of the central portion and extends adjacent inner surfaces of the pair of wings such that the free and looped ends are disposed above the u-shaped channel of the anvil buttress.

The surgical stapling apparatus may further include a cartridge buttress releasably disposed on the staple cartridge assembly of the end effector.

In embodiments, a method of loading the anvil buttress onto the end effector of the surgical stapling apparatus includes: sliding the anvil buttress of the anvil buttress retention system onto the anvil assembly of the end effector with the retention member in the untightened configuration; and pulling the free end of the retention member relative to and through the looped end to the tightened configuration.

According to another aspect of the present disclosure, a surgical stapling apparatus includes an end effector having an anvil assembly and a staple cartridge assembly, and an anvil buttress retention system releasably disposed on the anvil assembly. The anvil buttress retention system includes an anvil buttress, an adhesive layer disposed on an anvil facing surface of the anvil buttress, and a porous layer releasably disposed on a tissue facing surface of the anvil buttress. The surgical stapling apparatus may further include a cartridge buttress interconnected with the anvil buttress by a connecting member.

In embodiments, a method of loading the anvil buttress onto the end effector of the surgical stapling apparatus includes: positioning the adhesive layer of the anvil buttress retention system against a tissue facing surface of the anvil assembly; clamping the end effector such that the porous layer is compressed between the anvil and staple cartridge assemblies to secure the adhesive layer to the anvil assembly; unclamping the end effector; and removing the porous layer from the anvil buttress.

According to yet another aspect of the present disclosure, a surgical stapling apparatus includes an end effector having an anvil assembly and a staple cartridge assembly, and an anvil buttress retention system releasably disposed on the anvil assembly. The anvil assembly includes an anvil plate including a central longitudinal slot, a cover plate disposed over the anvil plate, and a proximally tapering passage disposed between the anvil plate and the cover plate. The anvil buttress retention system includes an anvil buttress and a tab extending proximally from a distal end of the anvil buttress. The tab is positioned within the proximally tapering passage of the anvil assembly such that a proximal portion of the tab is disposed adjacent the central longitudinal slot of the anvil plate. The tab may include an aperture configured to capture a portion of the anvil assembly therein.

The surgical stapling apparatus may further include a cartridge buttress connected to the anvil buttress by a connecting member to form a surgical buttress assembly having a substantially z-shaped configuration. In some embodiments, the connecting member includes a notch formed therein that is aligned with the central longitudinal slot of the anvil plate. The cartridge buttress may be releasably secured to the staple cartridge assembly by sutures.

In embodiments, a method of loading the anvil buttress onto the end effector of the surgical stapling apparatus includes: positioning the anvil buttress of the anvil buttress retention system against a tissue facing surface of the anvil assembly; and passing the tab through the proximally tapering passage of the anvil assembly to secure the proximal portion of the tab adjacent the central longitudinal slot of the anvil plate.

Other aspects, features, and advantages will be apparent from the description, drawings, and the claims.

BRIEF DESCRIPTION OF THE DRAWINGS

Various aspects of the present disclosure are described herein below with reference to the drawings, which are incorporated in and constitute a part of this specification, wherein:

FIG. 12 is a side view of a jaw assembly including a surgical buttress assembly releasably secured thereto in accordance with another embodiment of the present disclosure;

FIG. 13 is a cross-sectional view of a distal portion of an anvil assembly of the jaw assembly of FIG. 12;

FIG. 14 is a side view of the surgical buttress assembly of FIG. 12;

FIG. 15 is a top view of the surgical buttress assembly of FIGS. 12 and 14;

DETAILED DESCRIPTION OF THE EMBODIMENTS

Figure 1:
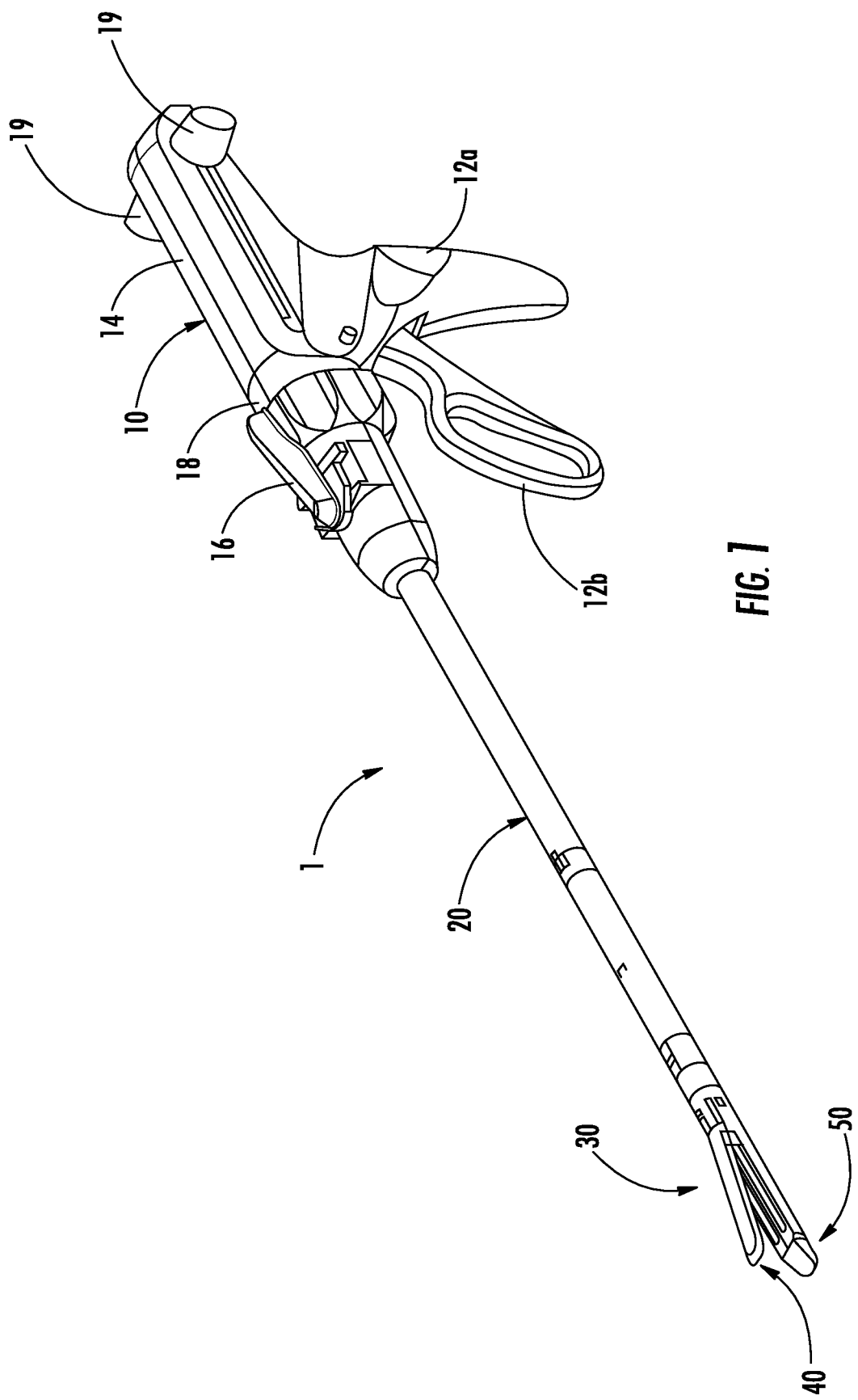
FIG. 1 is a perspective view of a surgical stapling apparatus in accordance with an embodiment of the present disclosure.

Various exemplary embodiments of the present disclosure are discussed herein below in terms of surgical buttresses for use with surgical stapling apparatus. The surgical buttresses described herein may be used in sealing a wound by approximating the edges of wound tissue between a staple cartridge assembly and an anvil assembly of a surgical stapling apparatus which includes at least one surgical buttress. The surgical buttress is releasably attached to the surgical stapling apparatus such that staples fired from the surgical stapling apparatus attach the surgical buttress to tissue. Thus, the present disclosure describes embodiments of surgical buttresses for reinforcing and sealing staple lines applied to tissue by surgical stapling apparatus.

Embodiments of the presently disclosed surgical buttress will now be described in detail with reference to the drawing figures wherein like reference numerals identify similar or identical elements. Throughout this description, the term "proximal" refers to a portion of a structure, or component thereof, that is closer to a user, and the term "distal" refers to a portion of the structure, or component thereof, that is farther from the user. Directional reference terms, such as "top," "bottom," "back," "side," and the like, are intended to ease description of the embodiments and are not intended to have any limiting effect on the ultimate orientations of a structure or any parts thereof.

Referring now to FIG. 1, an exemplary surgical stapling apparatus or surgical stapler 1 is shown for use in stapling tissue and applying one or more buttress materials or surgical buttresses to the tissue. The surgical stapling apparatus 1 generally includes a handle assembly 10, an elongate tubular body portion 20 extending distally from the handle assembly 10, and an end effector or jaw assembly 30 extending distally from the elongate tubular body portion 20. The jaw assembly 30 includes an anvil assembly 40 and a staple cartridge assembly 50. The jaw assembly 30 may be permanently affixed to the elongate tubular body portion 20 or may be detachable with respect to the elongate tubular body portion 20 and thus, replaceable with a new jaw assembly 30. The anvil assembly 40 and/or the staple cartridge assembly 50 is pivotable with respect to the elongate tubular body portion 20 such that the anvil and staple cartridge assemblies 40, 50 are movable between an open position in which the anvil and staple cartridge assemblies 40, 50 are spaced apart with respect to each other and a closed position in which the anvil and staple cartridge assemblies 40, 50 are substantially adjacent each other.

The handle assembly 10 includes a stationary handle member 12a, a movable handle member 12b, and a barrel portion 14. An articulation lever 16 is mounted on the forward end of the barrel portion 14 to facilitate articulation of the jaw assembly 30. A rotatable member 18 is also mounted on the forward end of the barrel portion 14, adjacent the articulation lever 16. Rotation of the rotatable member 18 relative to the barrel portion 14 rotates the elongate tubular body portion 20 and the jaw assembly 30 relative to the handle assembly 10 so as to properly orient the anvil and staple cartridge assemblies 40, 50 relative to tissue to be stapled. A pair of knobs 19 is movably positionable along the barrel portion 14. The pair of knobs 19 is advanced distally to approximate or close the anvil and staple cartridge assemblies 40, 50, relative to each other, and retracted proximally to unapproximate or open the anvil and staple cartridge assemblies 40, 50, with respect to each other. Actuation of the movable handle member 12*b* applies lines of staples 58 (FIG. 2) to tissue captured between the anvil and staple cartridge assemblies 40, 50.

Figure 2:
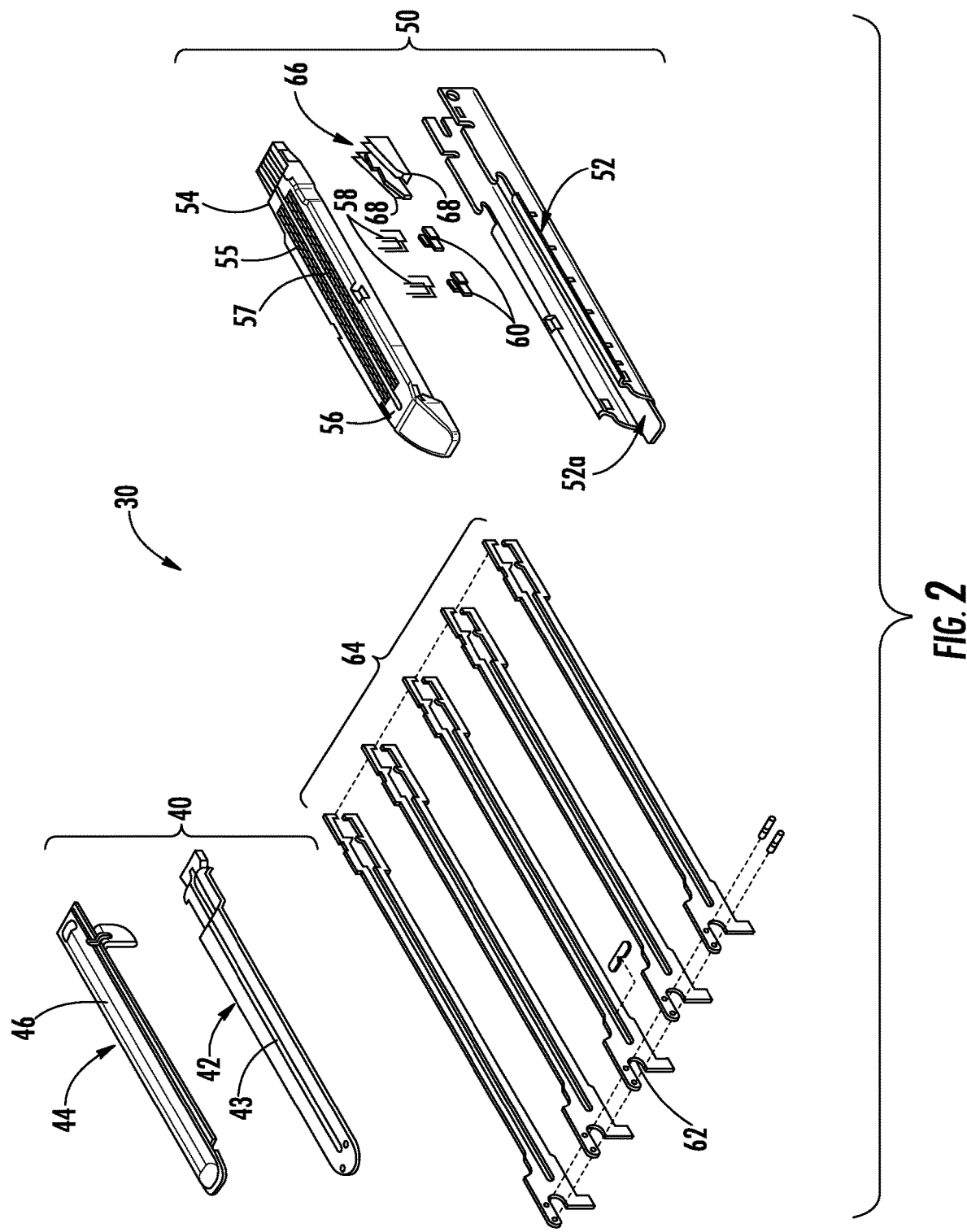
FIG. 2 is an exploded, perspective view of anvil and cartridge assemblies of a jaw assembly of the surgical stapling apparatus of FIG. 1.
Figure 3:
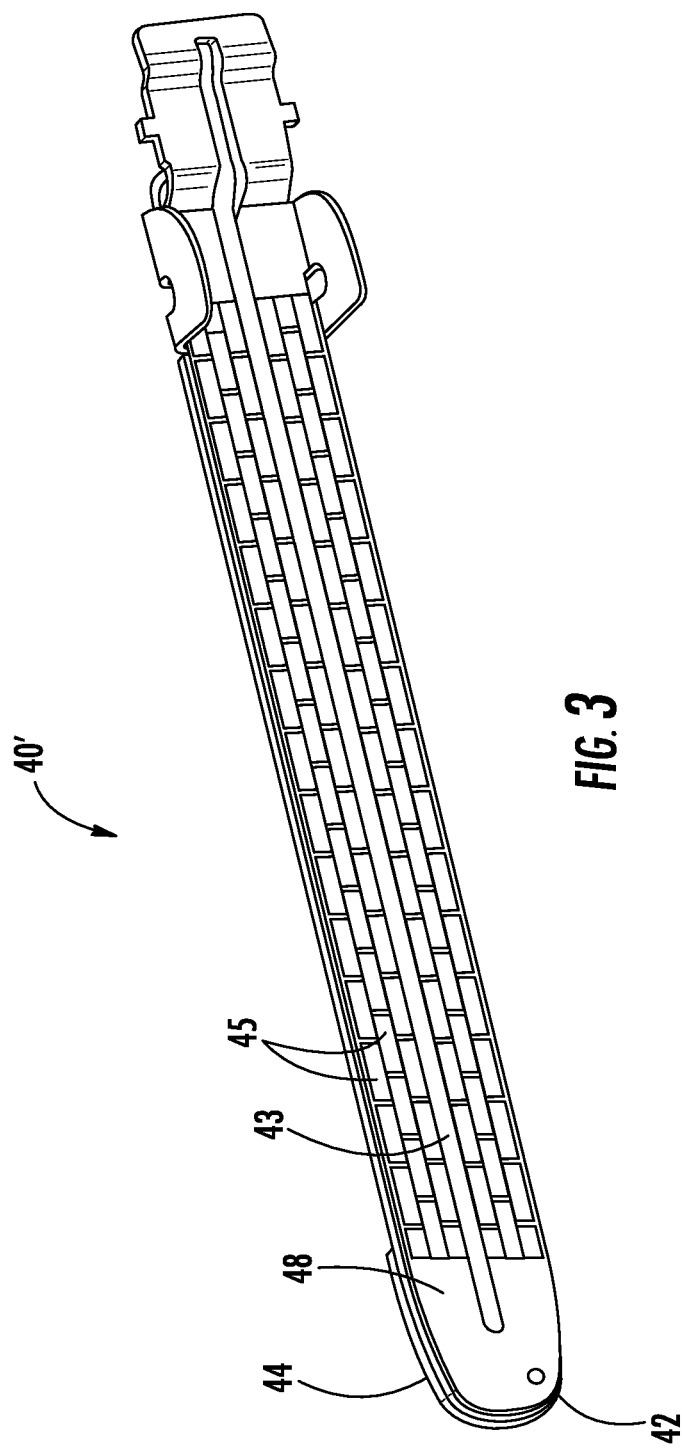
FIG. 3 is a bottom, perspective view of the anvil assembly of FIGS. 1 and 2.

As seen in FIG. 2, the anvil assembly 40 includes an anvil plate 42 having a central longitudinal slot 43 formed therein, and a cover plate 44 secured over the anvil plate 42 such that the cover plate 44 defines a top or outwardly facing surface 46 of the anvil assembly 40. As seen in FIG. 3, the anvil plate 42 includes a plurality of staple forming pockets/ cavities 45 defined in an inward or tissue facing surface 48 thereof.

With continued reference to FIG. 2, the cartridge assembly 50 includes a carrier 52 defining an elongated support channel 52*a* configured and dimensioned to selectively receive a staple cartridge 54 therein. The staple cartridge 54 is removable and replaceable in the carrier 52 of the staple cartridge assembly 50. The staple cartridge 54 includes an inward or tissue facing surface 56 defining staple pockets or retention slots 55 formed therein for receiving a plurality of fasteners or staples 58 and staple pushers 60. A central longitudinal slot 57 is formed in and extends along a substantial length of the staple cartridge 54 to facilitate passage of a knife blade 62 of a drive bar 64 therethrough. During operation of the surgical stapler 1, an actuation sled 66 translates through the staple cartridge 54 to advance cam wedges 68 of the actuation sled 66 into sequential contact with the staple pushers 60, to cause the staple pushers 60 to translate vertically within the staple pockets 55 and urge the staples 58 from the staple pockets 55 and into the staple forming cavities 45 of the anvil plate 42 of the anvil assembly 40.

For a detailed description of the structure and function of exemplary surgical stapling apparatus, reference may be made to U.S. Pat. Nos. 6,330,965, 6,241,139, and 7,819,896, the entire contents of each of which are incorporated herein by reference. It should be appreciated that principles of the present disclosure are equally applicable to surgical stapling apparatus having other configurations such as, for example, the types described in U.S. Pat. Nos. 7,128,253, 7,334,717, and 5,964,394, the entire contents of each of which are incorporated herein by reference. Accordingly, it should be understood that a variety of surgical stapling apparatus may be utilized with surgical buttresses of the present disclosure. For example, laparoscopic or open staplers, such as, for example, GIA™, Endo GIA™, TA™, and Endo TA™ staplers and/or linear and radial reloads with, for example, Tri-Staple™ technology, available through Medtronic (North Haven, Conn.) may be utilized with the surgical buttresses of the present disclosure.

Figure 4:
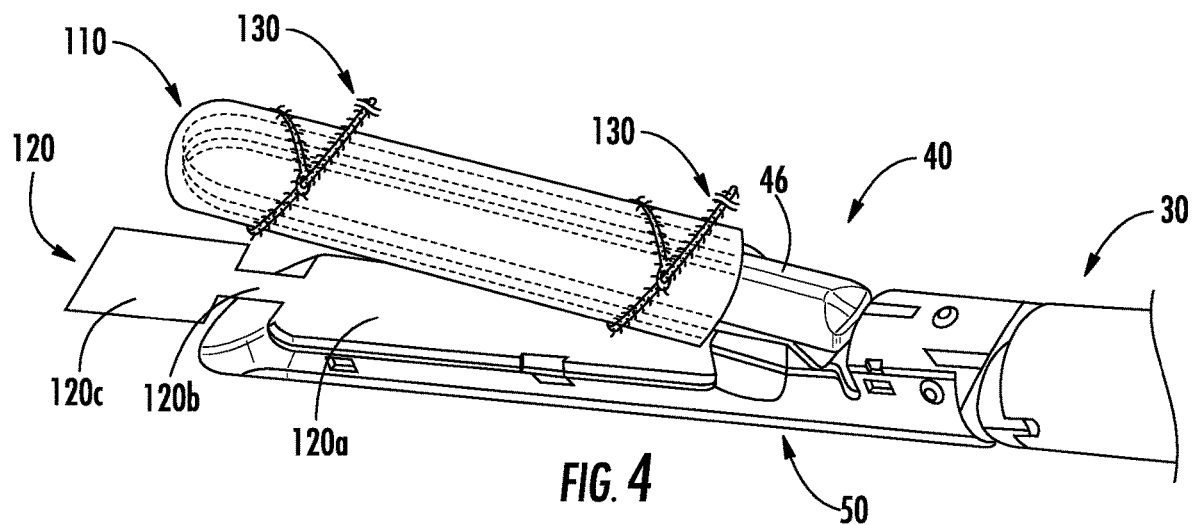
FIG. 4 is a perspective view of the jaw assembly of FIG. 1, including anvil and cartridge buttresses releasably secured thereto in accordance with an embodiment of the present disclosure.

With reference now to FIG. 4, surgical buttresses 110, 120 (also referred to herein as anvil buttress 110 and cartridge buttress 120) are releasably attached to the respective anvil and staple cartridge assemblies 40, 50 of the jaw assembly 30 of the surgical stapler 1 (FIG. 1). The surgical buttresses 110, 120 are fabricated from biocompatible materials which are bioabsorbable or non-absorbable, natural or synthetic materials. It should be understood that any combination of natural, synthetic, bioabsorbable, and/or non-bioabsorbable materials may be used to form the surgical buttresses 110, 120. The surgical buttresses 110, 120 may be formed from the same material or different materials.

The surgical buttresses 110, 120 may be porous, non-porous, or combinations thereof. Suitable porous structures include, for example, fibrous structures (e.g., knitted structures, woven structures, and non-woven structures) and/or foams (e.g., open or closed cell foams). Suitable non-porous structures include, for example, films. The surgical buttresses 110, 120 described herein may be a single porous or non-porous layer, or include a plurality of layers including any combination of porous and non-porous layers. For example, a surgical buttress may include multiple porous and non-porous layers that are stacked in an alternating manner. In another example, a surgical buttress may be formed in a "sandwich-like" manner wherein the outer layers of the surgical buttress are porous and the inner layer(s) are non-porous, or vice versa. The surgical buttresses 110, 120 may have the same or a different structure of layer(s).

Porous layer(s) in a surgical buttress may enhance the ability of the surgical buttress to absorb fluid, reduce bleeding, and seal the wound. Also, the porous layer(s) may allow for tissue ingrowth to fix the surgical buttress in place. Non-porous layer(s) in a surgical buttress may enhance the ability of the surgical buttress to resist tears and perforations during the manufacturing, shipping, handling, and stapling processes. Also, non-porous layer(s) may retard or prevent tissue ingrowth from surrounding tissues thereby acting as an adhesion barrier and preventing the formation of unwanted scar tissue.

It should be understood that while the surgical stapler 1 is shown including both the anvil and cartridge buttresses 110, 120, the surgical stapler 1 may include only the anvil buttress 110 or the cartridge buttress 120 depending on, for example, the surgical application and/or desired placement of the buttress material relative to tissue as should be understood by those skilled in the art. The anvil buttress 110 and/or the cartridge buttress 120 may be pre-loaded (e.g., by the manufacturer) onto the anvil assembly 40 and/or staple cartridge assembly 50 of the jaw assembly 30. Additional or replacement anvil buttresses 110 and/or cartridge buttresses 120 may be secured to the respective anvil and/or staple cartridge assemblies 40, 50 as needed or desired.

With continued reference to FIG. 4, the cartridge buttress 120 includes a body portion 120*a* configured to overlie at least a portion of the tissue facing surface 56 (FIG. 2) of the staple cartridge assembly 50, a neck portion 120*b* extending distally from the body portion 120*a*, and a head portion 120*c* extending distally from the neck portion 120*b*. For a detailed description of the structure and function of exemplary surgical buttress configurations suitable for use with the staple cartridge assembly 50, reference may be made to commonly owned U.S. Patent Appl. Pub. Nos. 2014/ 0138423 ("the '423 application") and 2013/0105548 ("the '548 application"), the entire contents of each of which are incorporated herein by reference.

The cartridge buttress 120 is releasably attached to the staple cartridge assembly 50 via any suitable attachment feature within the purview of those skilled in the art, such as, chemical attachment features (e.g., adhesives), mechanical attachment features (e.g., mounting structures, such as pins or straps), and/or attachment methods (e.g., welding). For a detailed description of exemplary attachment features suitable for use with the cartridge buttress 120, reference may be made to the '423 and '548 applications, the entire contents of each of which were previously incorporated herein by reference.

Figure 5:
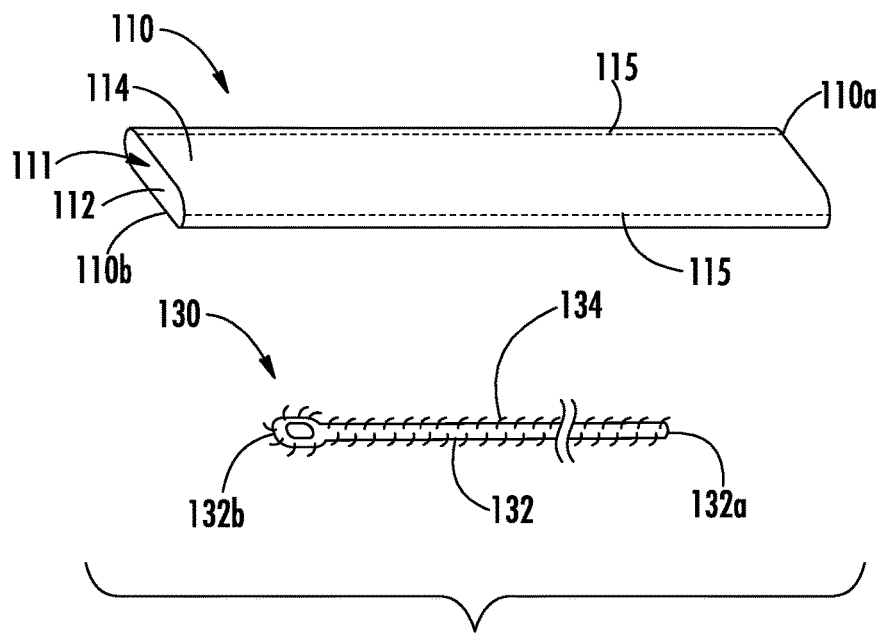
FIG. 5 is a perspective view, with parts separated, of an anvil buttress retention system including the anvil buttress of FIG. 4 and a retention member.

As shown in FIGS. 4 and 5, the anvil buttress 110 is in the form of a sleeve defining a cavity 111 therein that is configured to receive the anvil assembly 40 such that the anvil buttress 110 is disposed around the anvil assembly 40. Proximal and distal ends 110a, 110b of the anvil buttress 110 may be open to the cavity 111. In embodiments, the proximal end 110a of the anvil buttress 110 is open and configured to receive the anvil assembly 40, and the distal end 110b is closed and configured to contact a distal end of the anvil assembly 40 to prevent further proximal movement of the anvil buttress 110 relative to the anvil assembly 40.

The anvil buttress 110 includes a first layer 112 secured to a second layer 114 along respective lateral edges thereof to define the cavity 111 therebetween. In embodiments, the first and second layers 112, 114 are integrally formed from a single piece of buttress material that is shaped (e.g., rolled) to define the cavity 111 therein. In embodiments, perforations 115 are formed at the junction of the first and second layers 112, 114 to allow for the first layer 112 to separate from the second layer 114 after a stapling procedure is performed, as described in further detail below.

The anvil buttress 110 is slid proximally over the anvil assembly 40 such that the first layer 112 is positioned adjacent the tissue facing surface 48 (FIG. 3) of the anvil assembly 40, and the second layer 114 is positioned adjacent the top surface 46 of the anvil assembly 40. In some embodiments, the anvil buttress 110 has a pre-formed shape in which a lateral dimension of the cavity 111 is greater than a vertical dimension of the cavity 111 such that the anvil buttress 110 may be properly oriented on the anvil assembly 40.

With continued reference to FIGS. 4 and 5, the anvil buttress 110 is secured to the anvil assembly 40 by at least one retention member 130. The retention member 130 is fabricated from biocompatible materials which are any combination of natural, synthetic, bioabsorbable, and/or non-bioabsorbable materials. The retention member 130 includes an elongated body 132 having a free end 132a and a looped end 132b, and may be in the form of a suture, thread, filament, etc. The retention member 130 includes a plurality of barbs 134 extending from the elongated body 132 that are configured to grip the portion of the anvil buttress 110 over which it extends, as well as the looped end 132b when the free end 132a is passed therethrough to allow for quick assembly and securement of the retention member 130 and thus, the anvil buttress 110 to the anvil assembly 40. In embodiments, the plurality of barbs 134 are compound barbs. For a detailed description of the structure of exemplary compound barb configurations, reference may be made to U.S. Pat. No. 8,273,105, the entire contents of which are incorporated herein by reference.

It should be understood that while two retention members 130 are shown in FIG. 4, one on a proximal portion of the anvil buttress 110 and one on a distal portion of the anvil buttress 110, the number of retention members 130, and the placement of the retention members 130 relative to the anvil buttress 110, may vary. In embodiments, the retention members 130 are disposed on the anvil buttress 100 and extend across the central longitudinal slot 43 (FIG. 2) of the anvil assembly 40 such that actuation of the knife blade 62 (FIG. 2) results in severing of the retention members 130.

Figure 6A:
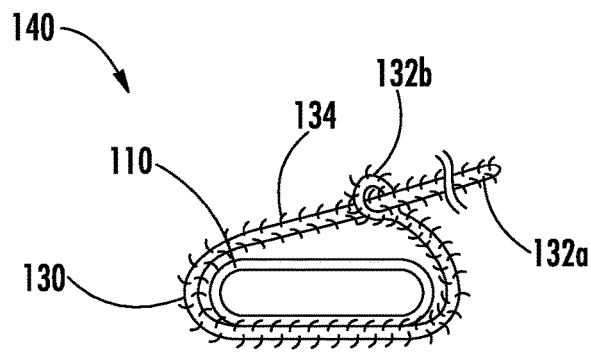
FIGS. 6A and 6B are end views of the anvil buttress retention system of FIG. 5 in pre-tightened and tightened configurations, respectively.
Figure 6B:
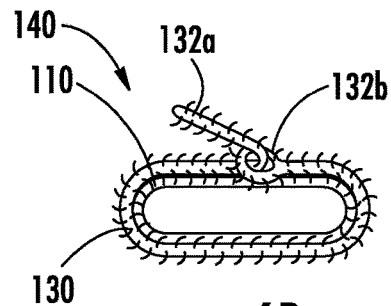

As shown in FIGS. 6A and 6B, the anvil buttress 110 and at least one retention member 130 are pre-assembled as an anvil buttress retention system 140 prior to positioning the anvil buttress 110 over the anvil assembly 40. As shown in FIG. 6A, the retention member 130 is pre-looped around the anvil buttress 110 with the free end 132a extending through the looped end 132b. The barbs 134 of the retention member 130 may aid in retaining the retention member 130 at a desired location along the length of the anvil buttress 110. In embodiments, the retention member 130 is attached to the anvil buttress 110 at a joint (e.g., on a tissue facing side of the anvil buttress 110) by, for example, using adhesives or welding the retention member 130 to the anvil buttress 110 to maintain the desired axial position of the retention member 130 along the length of the anvil buttress 110.

The anvil buttress retention system 140, in the untightened configuration shown in FIG. 6A, is slid over the anvil assembly 40 (FIG. 4), as described above. As shown in FIG. 6B, after the anvil buttress retention system 140 is placed on the anvil assembly 40 (FIG. 4), the free end 132a of the retention member 130 is pulled to tighten the retention member 130 around the anvil buttress 110 thereby securing the anvil buttress 110 to the anvil assembly 40.

In operation, with the anvil buttress retention system 140 loaded onto the anvil assembly 40, as described above, and the cartridge buttress 120 loaded onto the staple cartridge assembly 50, the surgical stapler 1 is used in accordance with methods known by those skilled in the art. Once the anvil and staple cartridge assemblies 40, 50 are clamped onto tissue (e.g., moved from the open position to the closed position), the surgical stapler 1 is fired. In firing the surgical stapler 1, the drive bar 64 is advanced distally through the jaw assembly 30 urging the staple pushers 60 upwardly which, in turn, drive the staples 58 out of the staple pockets 55 and through the anvil and cartridge buttresses 110, 120 as well as the captured tissue, thereby stapling the anvil and cartridge buttresses 110, 120 to the tissue.

During firing, the knife blade 62 of the drive bar 64 travels distally while substantially simultaneously cutting and dividing the tissue and anvil and cartridge buttresses 110, 120 disposed between the rows of now formed staples 58, as well as a portion of the retention member(s) 130 extending across the central longitudinal slot 43 of the anvil assembly 40 to free the anvil buttress 110 from the anvil assembly 40. When firing is complete, and the anvil and staple cartridge assemblies 40, 50 are unclamped, the anvil and cartridge buttresses 110, 120, which are now stapled to the tissue, pull away from the anvil and staple cartridge assemblies 40, 50 as the anvil and staple cartridge assemblies 40, 50 are withdrawn from within cavities 111 of the anvil and cartridge buttresses 110, 120. In embodiments, the first layer 112 of the anvil buttress 110 separates from the second layer 114 at the perforations 115 when the jaw assembly 30 is opened after performing the stapling procedure. It is understood that since the anvil buttress 110, the cartridge buttress 120 and the retention member(s) 130 are bioabsorbable they would be absorbed by the body over time.

Figure 7:
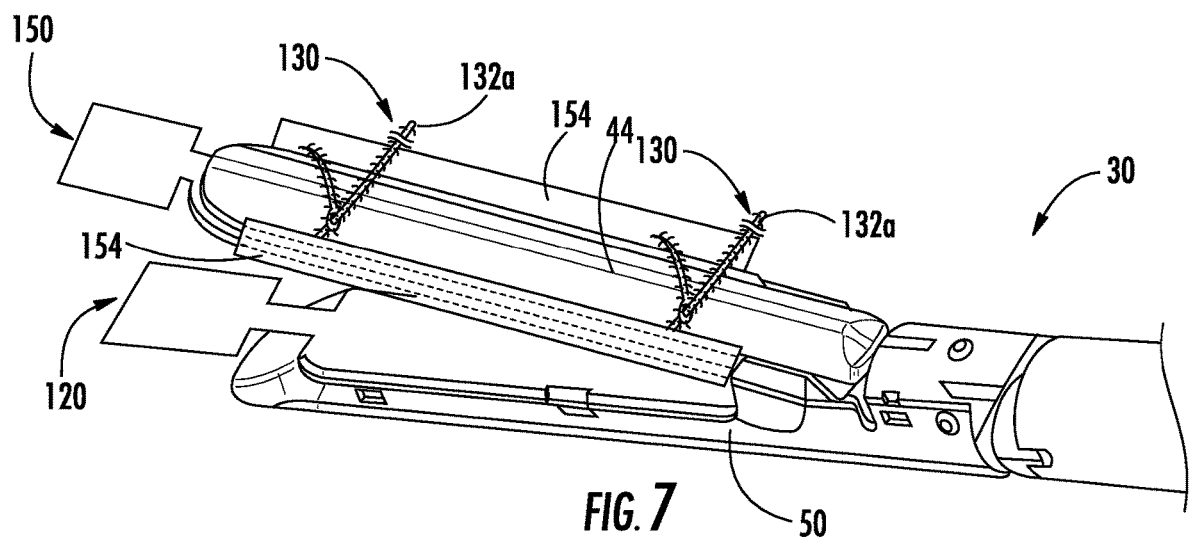
FIG. 7 is a perspective view of the jaw assembly of FIG. 1, including anvil and cartridge buttresses releasably secured thereto in accordance with another embodiment of the present disclosure.
Figure 8:
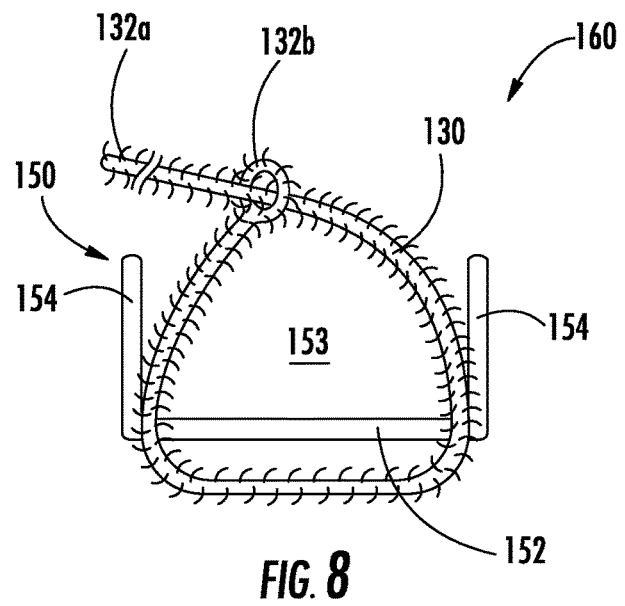
FIG. 8 is an end view of an anvil buttress retention system including the anvil buttress of FIG. 7 and a retention member.

Turning now to FIGS. 7 and 8, a jaw assembly 30 including a cartridge buttress 120 and an anvil buttress 150 in accordance with another embodiment of the present disclosure is shown. The anvil buttress 150 includes a body or central portion 152 and a pair of wings or side portions 154 extending vertically from side edges of the central portion 152 to define a substantially u-shaped channel 153 therebetween. The central portion 152 of the anvil buttress 150 is positioned adjacent the inward facing surface 48 (FIG. 2) of the anvil assembly 40 such that the anvil assembly 40 is positioned within the channel 153 of the anvil buttress 150. The pair of wings 154 are positioned adjacent sides of the anvil assembly 40 and extend upwardly past the cover plate 44 of the anvil assembly 40. The anvil buttress 150 is secured to the anvil assembly 40 by at least one retention member 130. As shown in FIG. 7, two retention members 130 secure the anvil buttress 150 to the anvil assembly 40, one on a proximal portion of the anvil buttress 150 and one on a distal portion of the anvil buttress 150.

The anvil buttress 150 and the at least one retention member 130 are pre-assembled as an anvil buttress retention system 160 prior to positioning the anvil buttress 150 on the anvil assembly 40. As shown in FIG. 8, the retention member 130 is pre-looped through side edges of the central portion 152 of the anvil buttress 150 and extends upwardly adjacent inner sides of the pair of wings 154 with the free end 132a of the retention member 130 extending through the looped end 132b above the channel 153 of the anvil buttress 150. After the anvil buttress retention system 160 is placed on the anvil assembly 40 as shown, for example, in FIG. 7 (e.g., by sliding the anvil buttress retention system 160 proximally onto the anvil assembly 40), the free end 132a of the retention member 130 is pulled to tighten the retention member 130 thereby securing the anvil buttress 150 to the anvil assembly 40.

During firing of a surgical stapler 1 including the anvil buttress retention system 160, distal movement of the knife blade 62 cuts and divides the captured tissue, the anvil buttress 150, as well as a portion of the retention member(s) 130 extending across the central longitudinal slot 43 of the anvil assembly 40 to free the anvil buttress 150 from the anvil assembly 40. When firing is complete, the jaw assembly 30 is moved to the open position and the anvil buttress 150 is pulled away from the anvil assembly 40.

Figure 9:
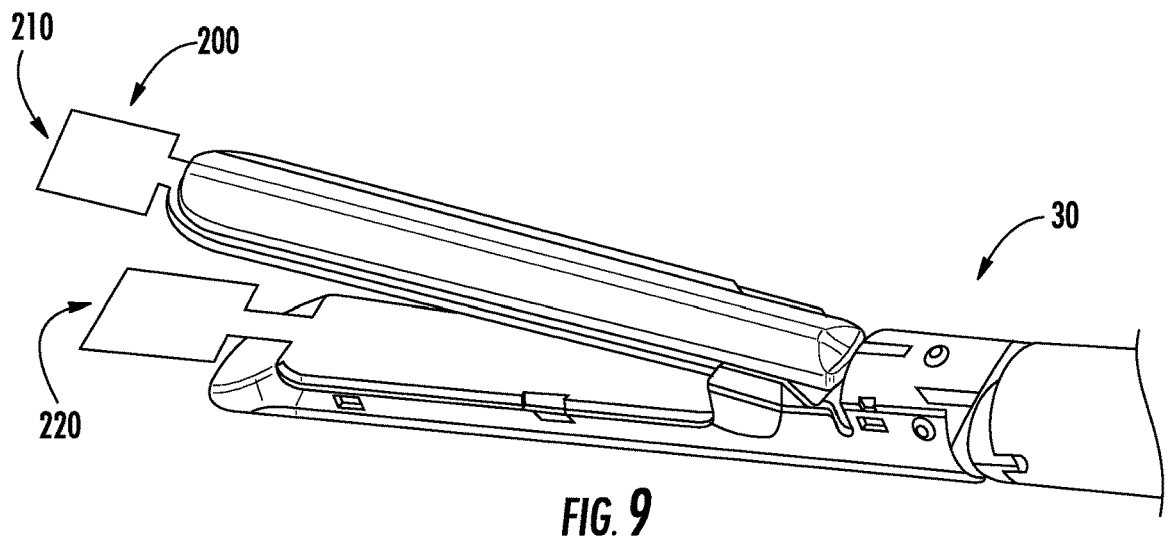
FIG. 9 is a perspective view of the jaw assembly of FIG. 1, including a surgical buttress assembly releasably secured thereto in accordance with an embodiment of the present disclosure.
Figure 10:
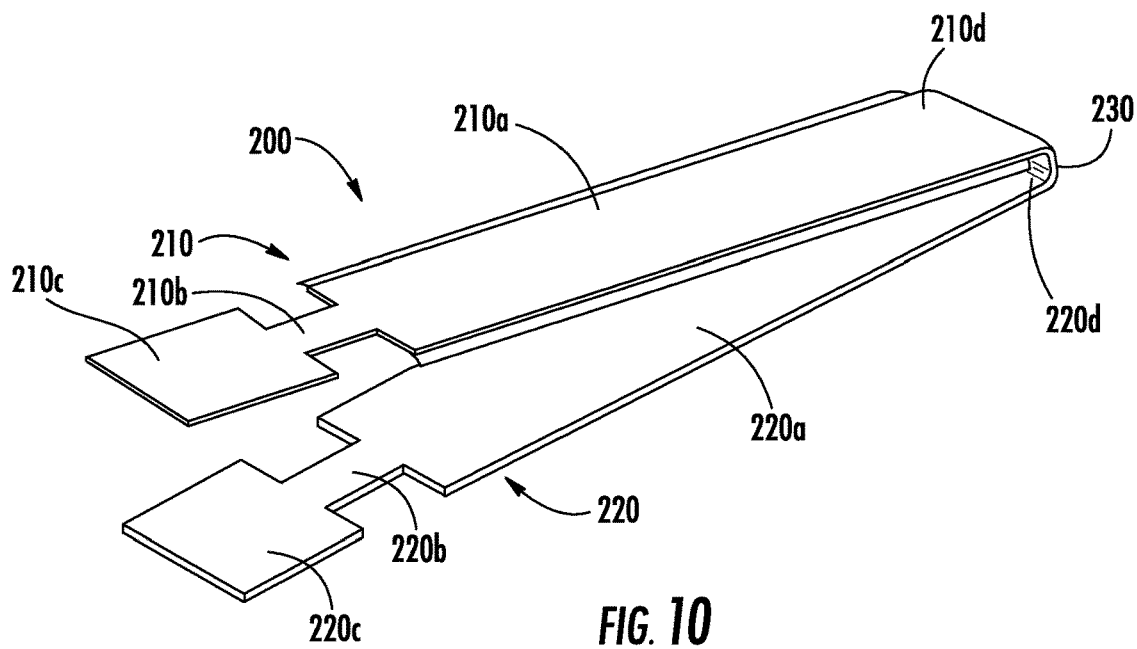
FIG. 10 is a perspective view of the surgical buttress assembly of FIG. 9.
Figure 11:
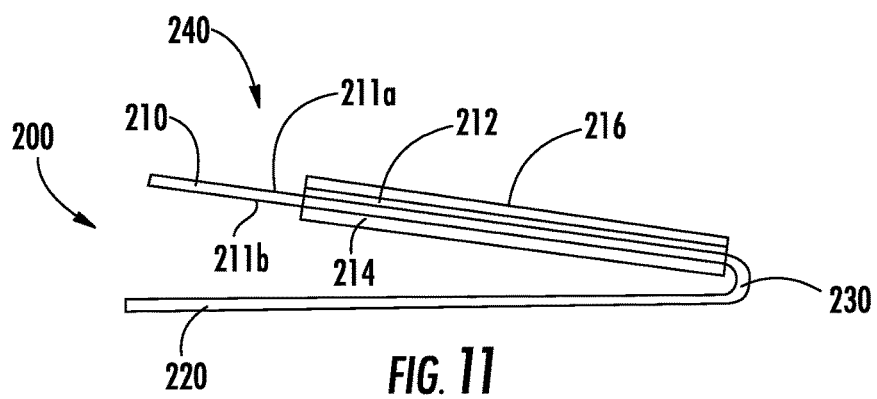
FIG. 11 is a side view of the surgical buttress assembly of FIGS. 9 and 10, including an anvil buttress retention system.

With reference now to FIGS. 9-11, a surgical buttress assembly 200 in accordance with an embodiment of the present disclosure is shown releasably disposed on a jaw assembly 30. The surgical buttress assembly 200 includes an anvil buttress 210 and a cartridge buttress 220 interconnected by a connecting member 230. It should be understood while both the anvil and cartridge buttresses 210, 220 are shown including a body portion 210a, 220a, a neck portion 210b, 220b, and a head portion 210c, 220c, the anvil and/or cartridge buttresses 210, 220 may have different configurations, as described above.

The connecting member 230 is attached to proximal ends 210d, 22d of the anvil and cartridge buttresses 210, 220. The connecting member 230 may be formed from the same material(s) as the anvil buttress 210 and/or the cartridge buttress 220, or may be formed from different material(s). The connecting member 230 may be, for example, a film or a web of fibrous material. In some embodiments, the connecting member 230 is formed from a rapidly degrading or rapidly absorbing polymer that degrades and/or is absorbed quickly upon implantation, thereby freeing the anvil and cartridge buttresses 210, 220 from each other.

The anvil buttress 210 is part of an anvil buttress retention system 240 which includes an adhesive layer 212 disposed on an anvil facing surface 211a of the anvil buttress 210 and a porous layer 214 releasably disposed on a tissue facing surface 211b of the anvil buttress 210. The porous layer 214 may be, for example, a sponge or a foam. In embodiments, the porous layer 214 is releasably attached to the anvil buttress 210 at one or more attachment points (e.g., adhesive attachment points). A release liner 216 may be disposed over the adhesive layer 212 prior to placement of the anvil buttress retention system 240 onto the anvil assembly 40.

In a method of loading the surgical buttress assembly 200 onto the jaw assembly 30, the cartridge buttress 220 is releasably attached to the staple cartridge assembly 50 via any suitable attachment feature, as described above. The release liner 216 is removed from the anvil buttress retention system 240 and the adhesive layer 212 is aligned and positioned against the tissue facing surface 48 (FIG. 2) of the anvil assembly 40. A clamping cycle is performed in which the anvil and staple cartridge assemblies 40, 50 are moved from the open position to the closed position and back to the open position. Upon movement to the closed position, the anvil and cartridge buttresses 210, 220 are compressed against opposed sides of the porous layer 214 to secure the adhesive layer 212 and thus, the anvil buttress 210 to the anvil assembly 40. The porous layer 214 may also cushion the anvil and cartridge buttresses 210, 220 during the clamping cycle to minimize any damage which may occur to the anvil and/or cartridge buttresses 210, 220. After re-opening the jaw assembly 30, the porous layer 214 is removed from the anvil buttress 210, rendering the jaw assembly 30 loaded and ready for use as shown, for example, in FIG. 9.

With reference now to FIG. 12, a surgical buttress assembly 300 in accordance with another embodiment of the present disclosure is shown releasably disposed on a jaw assembly 30'. The jaw assembly 30' is substantially similar to the jaw assembly 30 and will be described in detail herein to the extent necessary to describe the differences in construction and operation thereof. The jaw assembly 30' includes an anvil assembly 40' and a staple cartridge assembly 50. As shown in FIG. 13, the anvil assembly 40' includes an anvil plate 42' and a cover plate 44' which, together, define a proximally tapering passage 41' including a proximal junction 43' extending therein in which the anvil plate 42' and the cover plate 44' converge and/or define a minimal gap distance therebetween to releasably retain a tab 312 extending from an anvil buttress 310 in the anvil assembly 40', as described in further detail below.

As shown in FIGS. 14 and 15, the surgical buttress assembly 300 has a generally z-shaped configuration including an anvil buttress 310 and a tab 312, which together form the anvil buttress retention system 340, and a cartridge buttress 320 connected to the anvil buttress 310 by a connecting member 330. The tab 312 includes a proximal portion 312a, a central portion 312b including an aperture 313 formed therein, and a distal portion 312c. The connecting member 330 includes a notch 332 defined in a proximal end thereof that is axially aligned with the central longitudinal slots 43, 57 (FIG. 2) of the anvil and staple cartridge assemblies 40', 50. The notch 332 permits longitudinal reception of the knife blade 62 (FIG. 2) of the staple cartridge assembly 50 therethrough to reduce any bunching of the surgical buttress assembly 300 as the knife blade 62 is distally advanced during firing.

With reference again to FIGS. 12 and 13, the tab 312 extends through the passage 41' of the anvil assembly 40' and is secured therein by aligning the aperture 313 of the central portion 312b of the tab 312 with the proximal junction 43' of the anvil plate 42' and the cover plate 44' such that the proximal portion 312a of the tab 312 is positioned above and adjacent to the central longitudinal slot 43 (FIG. 2) of the anvil plate 42' and the distal portion 312c of the tab 312 is loosely retained within the passage 41'. The tab 312 may be secured to the anvil assembly 40' by threading the tab 312 through the passage 41' of the anvil assembly 40' or positioning the tab 312 around the anvil plate 42' prior to securing the cover plate 44' thereto. During firing of the surgical stapler 1, distal movement of the knife blade 62 (FIG. 2) cuts the proximal portion 312a of the tab 312 thereby freeing the anvil buttress 310 from the anvil assembly 40'.

The cartridge buttress 320 is releasably attached to the staple cartridge assembly 50 via any suitable attachment feature, as described above. In embodiments, the cartridge buttress 320 is releasably secured to the staple cartridge assembly 50 via sutures 350 that extend across the cartridge buttress 320 and are secured to side surfaces thereof. The sutures 350 also extend across the central longitudinal slot 57 (FIG. 2) of the staple cartridge assembly 50 such distal movement of the knife blade 62 (FIG. 2) cuts a portion of the suture 350 to free the cartridge buttress 320 from the staple cartridge assembly 50.

Figure 16:
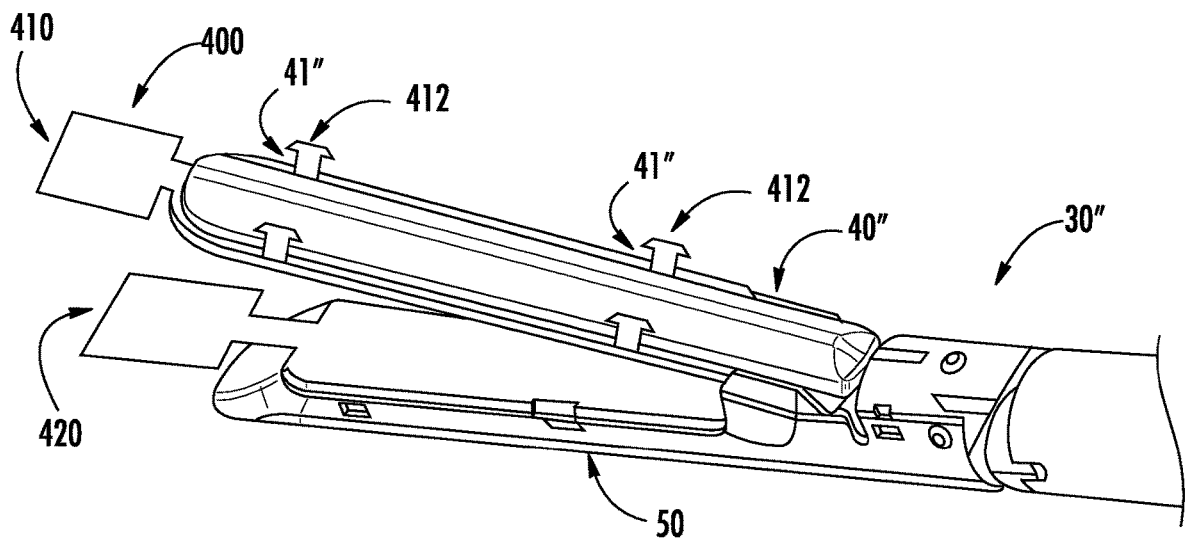
FIG. 16 is a perspective view of a jaw assembly including a surgical buttress assembly in accordance with yet another embodiment of the present disclosure.
Figure 17:
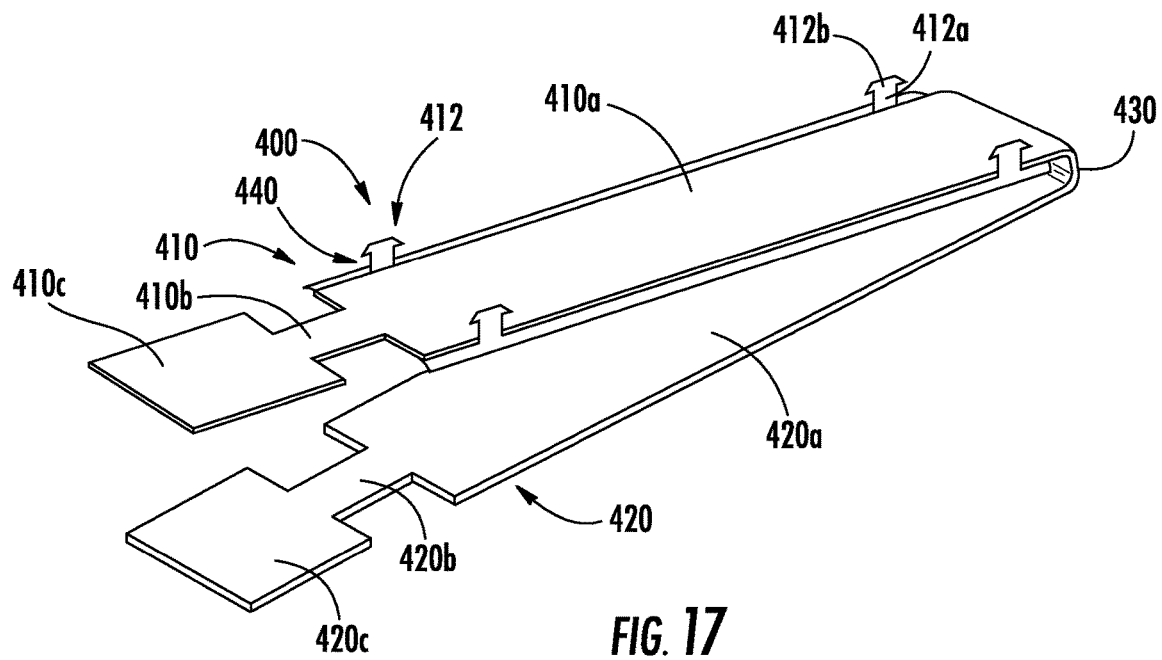
FIG. 17 is a perspective view of the surgical buttress assembly of FIG. 16.

With reference now to FIGS. 16 and 17, a surgical buttress assembly 400 in accordance with another embodiment of the present disclosure is shown loaded on a jaw assembly 30". The jaw assembly 30" is substantially similar to jaw assembly 30 except that the anvil assembly 40" defines one or more recesses or notches 41" formed in side surfaces thereof. The recesses 41" of the anvil assembly 40" are configured to selective couple an anvil buttress 410 to the anvil assembly 40", as described in further detail below.

The surgical buttress assembly 400 includes an anvil buttress 410 and a cartridge buttress 420 interconnected by a connecting member 430. The anvil and cartridge buttresses 410, 420 include a body portion 410a, 420a, a neck portion 410b, 420b, and a head portion 410c, 420c, however, as discussed above, other configurations are envisioned. The anvil buttress 410 and a plurality of tabs 412 define an anvil buttress retention system 440 of the surgical buttress assembly 400. The plurality of tabs 412 extend from opposed side edges of the anvil buttress 410. Each tab 412 includes a body 412a and an enlarged head 412b. The body 412a of the tab 412 is configured and dimensioned to be received and retained within one of the recesses 41" of the anvil assembly 40" (e.g., snapped into the recess 41"), with the enlarged head 412b disposed above the anvil assembly 40" to prevent movement of the anvil buttress 410 relative to the anvil assembly 40". The cartridge buttress 420 is secured to the staple cartridge assembly 50 via any suitable mechanism, as described above.

After firing of a surgical stapler including the jaw assembly 30" loaded with the surgical buttress assembly 400, re-opening the jaw assembly 30" after firing the surgical stapler provides sufficient force to separate the stapled anvil and cartridge buttresses 410, 420 from the anvil and staple cartridge assemblies 40", 50.

The surgical buttresses and anvil buttress retention systems described herein may also be configured for use with other surgical apparatus, such as electromechanical surgical devices as described, for example, in U.S. Patent Appl. Pub. Nos. 2015/0157320 and 2015/0157321, the entire contents of each of which are incorporated herein by reference.

Persons skilled in the art will understand that the systems, devices, and methods specifically described herein and illustrated in the accompanying figures are non-limiting exemplary embodiments, and that the description, disclosure, and figures should be construed merely exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another exemplary embodiment without departing from the scope of the present disclosure, and that such modifications and variations are also intended to be included within the scope of the present disclosure. Accordingly, the subject matter of the present disclosure is not to be limited by what has been particularly shown and described.

What is claimed is:

1. A surgical stapling apparatus comprising:
an end effector having an anvil assembly and a staple cartridge assembly; and
an anvil buttress retention system releasably disposed on the anvil assembly, the anvil buttress retention system including an anvil buttress and a retention member, the anvil buttress including a central portion positioned adjacent to a tissue facing surface of the anvil assembly and a pair of wings extending from the central portion and positioned adjacent to side surfaces of the anvil assembly to define a u-shaped channel configured to receive the anvil assembly therein, the retention member including an elongated body having a free end and a looped end, the elongated body looped around at least a portion of the anvil buttress, through side edges of the central portion, and extending adjacent inner surfaces of the pair of wings such that the free and looped ends are disposed above the u-shaped channel of the anvil buttress, the free end of the elongated body extendable through the looped end of the elongated body in an untightened configuration such that the anvil buttress retention system is slidable relative to the anvil assembly, the free end of the retention member movable relative to and through the looped end to a tightened configuration to secure the anvil buttress retention system to the anvil assembly.

2. A surgical stapling apparatus comprising:
an end effector having an anvil assembly and a staple cartridge assembly, the anvil assembly including an anvil plate including a central longitudinal slot, a cover plate disposed over the anvil plate, and a proximally tapering passage disposed between the anvil plate and the cover plate; and
an anvil buttress retention system releasably disposed on the anvil assembly, the anvil buttress retention system including an anvil buttress and a tab coupled to and extending proximally from a distal end of the anvil buttress, the anvil buttress positioned against a tissue facing surface of the anvil plate and the tab folded around a distal end of the anvil plate and positioned within the proximally tapering passage of the anvil assembly such that a proximal portion of the tab is disposed adjacent to the central longitudinal slot of the anvil plate; and
a cartridge buttress connected to the anvil buttress by a connecting member to form a surgical buttress assembly having a substantially z-shaped configuration, the connecting member including a notch formed therein, the notch aligned with the central longitudinal slot of the anvil plate.

3. The surgical stapling apparatus according to claim 2, wherein the tab includes an aperture configured to capture a portion of the anvil assembly therein.

4. The surgical stapling apparatus according to claim 2, wherein the cartridge buttress is releasably secured to the staple cartridge assembly by sutures.

5. A method of loading the anvil buttress onto the end effector of the surgical stapling apparatus of claim 2, the method including:
positioning the anvil buttress of the anvil buttress retention system against the tissue facing surface of the anvil plate; and
passing the tab through the proximally tapering passage of the anvil assembly to secure the proximal portion of the tab adjacent the central longitudinal slot of the anvil plate.

6. The surgical stapling apparatus according to claim 1, wherein the retention member includes a plurality of barbs.

7. The surgical stapling apparatus according to claim 1, further including a cartridge buttress releasably disposed on the staple cartridge assembly.

8. The surgical stapling apparatus according to claim 1, wherein the anvil assembly includes a central longitudinal slot, and the retention member extends across the central longitudinal slot of the anvil assembly.

9. The surgical stapling apparatus according to claim 1, wherein the retention member is a first retention member, and the anvil buttress retention system further includes a second retention member disposed in spaced relation relative to the first retention member along a length of the anvil buttress.

10. A method of loading the anvil buttress onto the end effector of the surgical stapling apparatus of claim 1, the method including:
    sliding the anvil buttress of the anvil buttress retention system onto the anvil assembly of the end effector with the retention member in the untightened configuration; and
    pulling the free end of the retention member relative to and through the looped end to the tightened configuration.

* * * * *